US007087577B2

(12) United States Patent
Benedict et al.

(10) Patent No.: US 7,087,577 B2
(45) Date of Patent: *Aug. 8, 2006

(54) METHOD OF PROMOTING NATURAL BYPASS

(75) Inventors: James J. Benedict, Arvada, CO (US); John P. Ranieri, Austin, TX (US); Marsha L. Whitney, Austin, TX (US); Rama Akella, Austin, TX (US)

(73) Assignee: Zimmer OrthoBiologies, Inc., Austin, TX (US)

( * ) Notice: Subject to any disclaimer, the term of this patent is extended or adjusted under 35 U.S.C. 154(b) by 588 days.

This patent is subject to a terminal disclaimer.

(21) Appl. No.: 09/748,038

(22) Filed: Dec. 22, 2000

(65) Prior Publication Data

US 2002/0040004 A1  Apr. 4, 2002

Related U.S. Application Data

(63) Continuation-in-part of application No. 09/173,989, filed on Oct. 16, 1998, now Pat. No. 6,211,157.

(51) Int. Cl.
*A61K 38/18* (2006.01)
(52) U.S. Cl. .................. 514/21; 514/8; 514/12
(58) Field of Classification Search ............... 530/350, 530/351, 395, 397, 399, 412, 414, 416, 422, 530/840; 514/2, 8, 12, 21; 424/549, 85.1
See application file for complete search history.

(56) References Cited

U.S. PATENT DOCUMENTS

| | | | |
|---|---|---|---|
| 4,529,590 A | 7/1985 | LeVeen et al. ................ 424/95 |
| 4,699,788 A | 10/1987 | Catsimpoolis et al. ...... 424/104 |
| 4,863,732 A | 9/1989 | Nathan et al. ................ 424/95 |
| 4,895,838 A | 1/1990 | McCluer et al. .............. 514/54 |
| 4,900,673 A | 2/1990 | Harper et al. ............... 435/199 |
| 4,950,483 A | 8/1990 | Ksander et al. ............. 424/422 |
| 5,116,738 A | 5/1992 | Wang et al. ................ 435/69.1 |
| 5,141,905 A | 8/1992 | Rosen et al. ............... 435/69.1 |
| 5,187,076 A | 2/1993 | Wozney et al. ............. 435/69.1 |
| 5,219,576 A | 6/1993 | Chu et al. .................... 424/484 |
| 5,270,300 A | 12/1993 | Hunziker ...................... 514/12 |
| 5,290,763 A | 3/1994 | Poser et al. ................... 514/21 |
| 5,318,957 A | 6/1994 | Cid et al. ....................... 514/8 |
| 5,328,695 A | 7/1994 | Lucas et al. ................. 424/426 |
| 5,371,191 A | 12/1994 | Poser et al. .................. 530/350 |
| 5,459,047 A | 10/1995 | Wozney et al. ............. 435/69.1 |
| 5,470,831 A | 11/1995 | Whitman et al. .............. 514/16 |
| 5,543,392 A | 8/1996 | Tomita et al. .................. 514/8 |
| 5,543,394 A | 8/1996 | Wozney et al. ............... 514/12 |
| 5,563,124 A | 10/1996 | Damien et al. ................ 514/21 |
| 5,595,722 A | 1/1997 | Grainger et al. ............. 424/9.2 |
| 5,616,490 A | 4/1997 | Sullivan et al. .............. 435/366 |
| 5,631,142 A | 5/1997 | Wang et al. ................ 435/69.1 |
| 5,635,372 A | 6/1997 | Celeste et al. .............. 435/69.1 |
| 5,637,480 A | 6/1997 | Celeste et al. .............. 435/69.4 |
| 5,656,587 A | 8/1997 | Sporn et al. .................... 514/2 |
| 5,661,007 A | 8/1997 | Wozney et al. ............. 435/69.4 |
| 5,677,276 A | 10/1997 | Dickerson et al. .............. 514/8 |
| 5,703,043 A | 12/1997 | Celeste et al. ................. 514/12 |
| 5,705,477 A | 1/1998 | Sporn et al. .................... 514/2 |
| 5,728,679 A | 3/1998 | Celeste et al. ................. 514/12 |
| 5,846,770 A | 12/1998 | LaVallie et al. ............ 435/69.1 |
| 5,849,880 A | 12/1998 | Wozney et al. .............. 530/399 |
| 5,854,207 A | 12/1998 | Lee et al. ........................ 514/2 |
| 5,866,364 A | 2/1999 | Israel et al. ................. 435/69.1 |
| 5,902,785 A | 5/1999 | Hattersley et al. .............. 514/2 |
| 5,928,940 A | 7/1999 | Sampath et al. ............. 435/325 |
| 5,932,216 A | 8/1999 | Celeste et al. ............. 424/158.1 |
| 5,965,403 A | 10/1999 | Celeste et al. .............. 435/69.4 |
| 5,972,884 A | 10/1999 | Cohen et al. ................. 514/12 |
| 5,981,489 A | 11/1999 | Stevenson et al. ............ 514/15 |
| 5,994,094 A | 11/1999 | Hotten et al. ............... 435/69.1 |
| 6,051,648 A | 4/2000 | Rhee et al. ................. 525/54.1 |
| 6,120,760 A | 9/2000 | Hötten et al. ............... 424/85.1 |
| 6,124,273 A | 9/2000 | Drohan et al. ................ 514/55 |
| 6,150,328 A | 11/2000 | Wang et al. .................. 514/12 |
| 6,177,406 B1 | 1/2001 | Wang et al. .................. 514/12 |
| 6,197,550 B1 | 3/2001 | Hötten et al. ............... 435/69.5 |
| 6,211,157 B1 | 4/2001 | Benedict et al. .............. 514/21 |
| 6,372,257 B1 * | 4/2002 | Marchosky ................. 424/488 |
| 6,468,960 B1 | 10/2002 | Lukanidin et al. .............. 514/2 |
| 6,498,142 B1 | 12/2002 | Sampath et al. .............. 514/12 |
| 2002/0025340 A1 | 2/2002 | Dyer .......................... 424/486 |
| 2003/0022828 A1 | 1/2003 | Akella et al. ................. 514/12 |
| 2003/0104977 A1 * | 6/2003 | Ripamonti et al. ............. 514/2 |

FOREIGN PATENT DOCUMENTS

CN  1163780 A  * 11/1997

(Continued)

OTHER PUBLICATIONS

Ramoshebi et al. Osteogenic Protein-1, a Bone Morphogenetic Protein . . . The Anatomical Record. May 1, 2000, vol. 259, pp. 97-107.*

B. Schumacher, et al, "Induction of Neoangiogenesis in Ischemic Myocardium by Human Growth Factors", Clincial Investigation and Reports, American Heart Association 645-650 (1998).

(Continued)

*Primary Examiner*—Jeffrey Edwin Russel
(74) *Attorney, Agent, or Firm*—William, Morgan & Amerson, P.C.

(57) ABSTRACT

An angiogenic factor comprising a mixture of proteins derived from bone. The angiogenic protein mixture is produced by a series of steps that allow the proteins to be kept in solution. The angiogenic mixture of bone proteins is produced by a multi-step process that includes at least one ultrafiltration step, an anion exchange chromatography step, a cation exchange chromatography step and a high performance liquid chromatography (HPLC) purification step.

32 Claims, 43 Drawing Sheets

FOREIGN PATENT DOCUMENTS

| EP | 0433225 B1 | 6/1991 |
|---|---|---|
| EP | 0516901 A1 | 12/1992 |
| EP | 0747066 B1 | 12/1996 |
| WO | WO 97/41880 | 11/1997 |
| WO | WO 99/02674 | 1/1999 |
| WO | WO 99/31136 | 6/1999 |
| WO | WO 99/57146 | 11/1999 |
| WO | WO 02/00244 | 1/2002 |
| WO | WO 02/47713 | 6/2002 |
| WO | WO 03/060076 | 7/2003 |

OTHER PUBLICATIONS

Jamie P. Levine, et al, "Bone Morphogenetic Protein Promotes Vascularization and Osteoinduction in Preformed Hydroxyapatite in the Rabbit", Annals of Plastic Surgery, vol. 39, 158-168 (1997).

Hidetoshi Yamashita, et al "Growth/Differentiation Factor-5 Induces Angiogenesis in Vivo", Experimental Cell Research 235, 218-226 (1997).

Takashi Nakaoka et al, "Inhibition of Rat Vascular Smooth Muscle Proliferation in Vitro and In Vivo by Bone Morphogenetic Protein-2", Journal of Clinical Investigation 100, 2824-2832 (1997).

Judah Folkman, "Angiogenic Therapy of the Human Heart", American Heart Association, Inc., 628-629, (1998).

Cuevas et al., "Fibroblast Growth Factor Protects the Kidney Against Ischemia-Reperfusion Injury," *Eur. J. Med. Res.*, 4:403-10, 1999.

Freed et al., "Neocartilage formation in vitro and in vivo using cells cultured on synthetic biodegradable polymers," *J. Biomed. Mater. Res.*, 27:11-23, 1993.

Freedman and Isner, "Therapeutic Angiogenesis for Ischemic Cardiovascular Disease," *J. Molecular and Cellular Cardiology*, 33:379-93, 2001.

Hammerman, "Growth Factors in Renal Development," *Seminars in Nephrology*, 15:291-99, 1995.

Hirschberg et al., "Multicenter clinical trial of recombinant human insulin-like growth factor I in patients with acute renal failure," *Kidney International*, 55:2423-32, 1999.

Kawa-uchi et al., "Fibroblast growth factor enhances expression of TGFβ-stimulated-clone-22 gene in osteoblast-like cells," *Endocrine*, 3:833-37, 1995.

Laham et al., "Intrapericardial Delivery of Fibroblast Growth Factor-2 Induces Neovascularization in a Porcine Model of Chronic Myocardial Ischemia," *J. Pharmacol. Exp. Ther.*, 292:795-802, 2000.

Mueller et al., "Myocardial angiogenesis induction with bone protein derived growth factors (animal experiment)," *Swiss Med. Wkly*, 131:23-25, 2001.

Nishida et al., "Adenovirus-Mediated Gene Transfer to Nucleus Pulposus Cells," *Spine*, 23:2437-42, 1998.

Parsons-Wingerter et al., "A novel assay of angiogenesis in the quail chorioallantoic membrane: stimulation by bFGF and inhibition by angiostatin according to fractal dimension and grid intersection," *Microvasc. Res.*, 55:201-14, 1998.

Prochazka et al., "Epidermal Growth Factor and Insulin Growth Factor 1 Increase FSH-Stimulated Expansion of Porcine Cumulus Cells in Serum-free Medium," *J. Reproduction and Fertility*, 25:64, 2000.

Sakaguchi et al., "A Combination of EGF and IGF-1 Accelerates the Progression of Meiosis in Bovine Follicular Oocytes In Vitro and Fetal Calf Serum Neutralizes the Acceleration Effect," *Theriogenology*, 54:1327-42, 2000.

Stelnicki et al., "Bone Morphogenetic Protein-2 Induces Scar Formation and Skin Maturation in the Second Trimester Fetus," *Plastic and Reconstructive Surgery*, 101:12-19, 1998.

Vukicevic et al., "Osteogenic Protein-1 (Bone Morphogenetic Protein-7) Reduces Severity of Injury After Ischemic Acute Renal Failure in Rat," *J. Clin. Invest.*, 102:202-14, 1998.

Wiley and Cunningham, "Epidermal Growth Factor Stimulates Fluid Phase Endocytosis in Human Fibroblasts Through a Signal Generated at the Cell Surface," *J. Cellular Biochem.*, 19:383-94, 1982.

Yamamoto et al., "Histologic evidence that basic fibroblast growth factor enhances the angiogenic effects of transmyocardial laser revascularization," *Basic Res. Cardiol.*, 95:55-63, 2000.

Yonggang et al., "Percutaneous injection of bone morphogenetic protein and polyvinyl pyrrolidone composite," *J. Xi' an Medical University*, 22:132-33, 2001.

* cited by examiner

| Band No. | Identity |
|---|---|
| 1 | Histone H1.c |
| 2 | Histone H1.c |
| 3 | Ribosomal protein RS20 |
| 4 | Similar to ribosomal protein LORP |
| 5 | BMP-3 |
| 6 | α2 macroglobulin RAP and BMP-3 |
| 7 | Similar to ribosomal protein LORP |
| 8 | BMP-3 |
| 9 | BMP-3 |
| 11 | Ribosomal protein RL6 and BMP-3 |
| 18 | TGF-β2/SPP24 |
| 20 | Factor H |
| 22 | TGF-β2 |
| 25 | BMP-3 and H1.x |
| 29 | BMP-3 and ribosomal protein RL32 |

Antibody Listing

| Specificity | Antigen | Host Species | PC/MC | Source | Catalog No. |
|---|---|---|---|---|---|
| TGF-β1 (human) | Protein | Rabbit | Polyclonal | Promega | G1221 |
| TGF-β2 (human) | Peptide | Rabbit | Polyclonal | Santa Cruz Biotechnology | sc-90 |
| TGF-β3 (human) | Peptide | Rabbit | Polyclonal | Santa Cruz Biotechnology | sc-82 |
| BMP-2 (human) | Protein | Rabbit | Polyclonal | Austral Biologics | PA-513-9 |
| BMP-3 (human) | Peptide | Chicken | Polyclonal | Research Genetics | NA |
| BMP-4 (human) | Peptide | Goat | Polyclonal | Santa Cruz Biotechnology | sc-6896 |
| BMP-5 (human) | Peptide | Goat | Polyclonal | Santa Cruz Biotechnology | sc-7405 |
| BMP-6 (human) | Peptide | Mouse | Monoclonal | Novacastra Laboratories | NCL-BMP6 |
| BMP7 (human) | Peptide | Rabbit | Polyclonal | Research Genetics | NA |
| FGF-1 (human) | Peptide | Goat | Polyclonal | Santa Cruz Biotechnology | sc-1884 |
| osteonectin (bovine) | Protein | Mouse | Polyclonal | DSHB | AON-1 |
| osteocalcin (bovine) | Protein | Rabbit | Polyclonal | Accurate Chemicals | A761/R1H |
| serum albumin (bovine) | Protein | Rabbit | Polyclonal | Chemicon International | AB870 |
| transferrin (human) | Protein | Chicken | Polyclonal | Chemicon International | AB797 |
| apo-A1 lipoprotein (human) | Protein | Goat | Polyclonal | Chemicon International | AB740 |

FIG.14

Identification of Proteins by Amino Acid Sequencing of Tryptic Fragments from 1D Gels

| Band | Sample | Sequence Data | Best Database Match | Match | Identification | Species | Accession No. | AAs |
|---|---|---|---|---|---|---|---|---|
| 1 | | | | | | | | |
| 2 | fx 49 (1579) | XLAAAGYDVEK | ALAAAGYDVEK | 11/11 | histone H1.c | human | 87668 (NCBI) | 65–75 |
| 3 | fx 67 (1346) | SLEKVCADLIR | SLEKVCADLIR | 11/11 | 40s Ribosomal Protein S20 | rat | R3RT20 (PIR) | 31–41 |
| 4 | fx 65 () | (V)VCGMLGFPSEAPV | WCGMLGFPGEKRV | 11/14 | LORP | mouse | AAC95338 (NCBI) | 213–226 |
| 5 | N terminal seq | STGVLLPLQNNELPG | STGVLLPLQNNELPG | 15/15 | BMP-3 | human | 4557371 (NCBI) | 290–304 |
|   | fx 72 (3925) | STGVLLPLQNNELPGAEYQY | STGVLLPLQNNELPGAEYQY | 20/20 | BMP-3 | human | 4557371 (NCBI) | 290–309 |
|   | fx 74 (3409) | STGVLLPLQ | STGVLLPLQ | 9/9 | BMP-3 | human | 4557371 (NCBI) | 290–298 |
| 6 | fx 55 (1566) | (S)QTLQFXE | SQTLQFDE | 7/8 | BMP-3 | human | 4557371 (NCBI) | 346–353 |
|   | fx 47 | VYAF | no match | | ??? | | | |
|   | N terminal seq | HAGKYSREKNT(P)A(P) | HGGKYSREKNQPKP | 11/14 | α2-Macroglobulin Receptor Assoc. Pro. | human | P30533 (Swiss-Prot) | 31–46 |
|   | fx 57 (1438) | SQTLQFDEQ | SQTLQFDEQ | 9/9 | BMP-3 | human | 4557371 (NCBI) | 346–354 |
|   | fx 57 (1652) | SLKPSNHA | SLKPSNHA | 8/8 | BMP-3 | human | 4557371 (NCBI) | 410–417 |
| 7 | fx 51 (1093) | AALRPLVKP | AALRPLVKP | 9/9 | 60s Ribosomal Protein L32 | mouse | P17932 (Swiss-Prot) | 1–9 |
|   | fx 37 (no MS) | A(H)I(Q)VERYV | AVER | 5/5 | 60s Ribosomal Protein L32 | mouse | P17932 (Swiss-Prot) | 109–113 |
|   | fx 37 (no MS) | A(H)I(Q)VERYV | HQSDRYV | 5/7 | 60s Ribosomal Protein L32 | mouse | P17932 (Swiss-Prot) | 22–28 |
| 8 | fx 78 () | XALF(G)AQLGXALGPI | no match | | ??? | | | |
| 9 | fx 56 (1567) | SQTLQFDEQT | SQTLQFDEQT | 10/10 | BMP-3 | human | P12645 (Swiss-Prot) | 346–355 |

FIG. 15A

Identification of Proteins by Amino Acid Sequencing of Tryptic Fragments from 1D Gels

| Band | Sample | Sequence Data | Best Database Match | Match | Identification | Species | Accession No. | AAs |
|---|---|---|---|---|---|---|---|---|
| 11 | fx 55 (1311) | SQTLXF | SQTLQF | 5/6 | BMP-3 | human | 4557371 (NCBI) | 346-351 |
|  | fx 47 (1772) | VLATVTKPVGGDK | VLATVTKPVGGDK | 13/13 | 60s Ribosomal Protein L6 | human | Q02878 (Swiss-Prot) | 87-99 |
|  | fx 76 (1795) | xVFAL | VFAL | 4/4 | 60s Ribosomal Protein L6 | human | Q02878 (Swiss-Prot) | 273-276 |
|  | fx 61 (1145) | AIPQLQGYLR | AIPQLQGYLR | 9/10 | 60s Ribosomal Protein L6 | human | Q02878 (Swiss-Prot) | 262-271 |
| 18 |  |  |  |  |  |  |  |  |
| 22 | fx 58 (1101) | ALDAAYCFR | ALDAAYCFR | 9/9 | TGF-β2 | human | P08112 (Swiss-Prot) | 303-311 |
|  | fx 69 (no match) | GYNANFCAGACPYL | GYNANFCAGACPYL | 14/14 | TGF-β2 | human | P08112 (Swiss-Prot) | 340-353 |
|  | fx 66 (1411.71) | VNSQSLSPY | VNSQSLSPY | 9/9 | SPP24 | bovine | Q27967 (Swiss-Prot) | 42-50 |
| 25 | fx 39(1470) | KAAKPSV(P) | KAAKPSVP | 8/8 | histone H1 x | human | JC4928 (PIR) | 199-206 |
| 29 |  |  |  |  |  |  |  |  | fx=fraction number (molecular weight of fragment, as measured by SDS-PAGE)

FIG. 15B

Identification of Proteins by Mass Spectrometry of Tryptic Fragments from 1D Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 1 | 4 peaks match with histone H1.c | human | 87668 (NCBI) | 1172.97 | 1172.37 | 0.60 | 110-121 | 22 | 15 MS peaks match with Band 2 |
|  |  |  |  | 1579.87 | 1579.71 | 0.16 | 65-79 |  |  |
|  |  |  |  | 1708.47 | 1707.89 | 0.58 | 64-79 |  |  |
|  |  |  |  | 2011.58 | 2012.32 | -0.74 | 35-54 |  |  |
| 2 | 3 peaks match with histone H1.c | human | 87668 (NCBI) | 1579.76 | 1579.71 | 0.05 | 65-79* | 16 | identification of starred peptide confirmed by sequence analysis |
|  |  |  |  | 1708.02 | 1707.89 | 0.13 | 64-79 |  | 15 MS peaks match with Band 1 |
|  |  |  |  | 2012.12 | 2012.32 | -0.20 | 35-54 |  |  |
| 3 | 7 peaks match with ribosome S20 | rat | R3RT20 (PIR) | 1129.76 | 1129.40 | 0.36 | 50-59 | 62 |  |
|  |  |  |  | 1156.21 | 1156.30 | -0.09 | 76-83 |  |  |
|  |  |  |  | 1334.46 | 1334.62 | -0.16 | 56-66 |  |  |
|  |  |  |  | 1352.13 | 1351.58 | 0.55 | 88-99 |  |  |
|  |  |  |  | 1518.04 | 1517.77 | 0.27 | 9-21 |  |  |
|  |  |  |  | 1919.02 | 1919.19 | -0.17 | 5-21 |  |  |
|  |  |  |  | 3404.02 | 3404.87 | -0.85 | 88-119 |  |  |
| 4 | 3 peaks match with Lysyl Oxidase RP | human | NP002309 (Swiss-Prot) | 1987.95 | 1988.27 | -0.32 | 150-167 | 6 | 12 MS peaks match with Band 8 |
|  |  |  |  | 2410.35 | 2410.63 | -0.28 | 648-669 |  |  |
|  |  |  |  | 2610.57 | 2610.10 | 0.47 | 455-478 |  |  |

FIG.16A

Identification of Proteins by Mass Spectrometry of Tryptic Fragments from ID Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 5 | 9 peaks match with BMP-3 | human | 4557371 (NCBI) | 1113.32 | 1113.31 | 0.01 | 361-368 | 48 | % coverage calculation is relative to the mature BMP-3, 183 AAS (290-472) |
| | | | | 1438.53 | 1438.58 | -0.05 | 346-357 | | |
| | | | | 1566.76 | 1566.76 | 0.00 | 345-357 | | |
| | | | | 1651.86 | 1651.91 | -0.05 | 410-424 | | |
| | | | | 1794.09 | 1794.02 | 0.07 | 346-360 | | |
| | | | | 2268.46 | 2268.63 | -0.17 | 374-392 | | |
| | | | | 2424.45 | 2424.81 | -0.36 | 373-392 | | |
| | | | | 3409.15 | 3407.77 | 1.38 | 290-318* | | identification of starred peptide confirmed by sequence analysis |
| 6 | 3 peaks match with α2-Macroglobulin RAP | human | P30533 (Swiss-Prot) | 1002.24 | 1002.15 | 0.09 | 283-290 | 17 | |
| | | | | 2362.58 | 2362.43 | 0.15 | 129-150 | | |
| | | | | 3048.51 | 3048.52 | -0.01 | 257-282 | | |
| | 2 peaks match with BMP-3 | human | 4557371 (NCBI) | 1566.93 | 1566.75 | 0.18 | 346-357 | 15 | % coverage calculation is relative to the mature BMP-3, 183 AAS (290-472) |
| | | | | 1651.88 | 1651.91 | -0.03 | 410-424 | | |

FIG. 16B

Identification of Proteins by Mass Spectrometry of Tryptic Fragments from ID Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 7 | 4 peaks match with mouse ribosome L32 | mouse | P17932 (Swiss-Prot) | 1033.25 | 1033.17 | 0.08 | 67-75 | 33 | |
| | | | | 1093.31 | 1093.40 | -0.09 | 1-10* | | |
| | | | | 1134.72 | 1134.28 | 0.44 | 65-74 | | |
| | | | | 1449.78 | 1449.66 | 0.12 | 19-29 | | |
| | 5 peaks match with BMP-3 | human | 4557371 (NCBI) | 1060.42 | 1060.20 | 0.22 | 102-111 | 21 | % coverage calculation is relative to the mature BMP-3, 183 AAS (290-472) |
| | | | | 1113.39 | 1113.31 | 0.08 | 361-368 | | |
| | | | | 1360.26 | 1360.58 | -0.32 | 190-200 | | |
| | | | | 1652.28 | 1651.91 | 0.37 | 410-424 | | |
| | | | | 1793.62 | 1794.02 | -0.40 | 346-360 | | |
| 8 | 1 peak match with Lysyl Oxidase RP | human | NP002309 (Swiss-Prot) | 2410.37 | 2410.63 | -0.26 | 648-669 | 3 | |
| 9 | 6 peaks match with BMP-3 | human | 4557371 (NCBI) | 1113.14 | 1113.31 | -0.17 | 361-368 | 36 | 12 MS peaks match with Band 4 |
| | | | | 1438.60 | 1438.58 | 0.02 | 346-357 | | % coverage calculation is relative to the mature BMP-3, 183 AAS (290-472) |
| | | | | 1566.77 | 1566.76 | 0.01 | 345-357 | | |
| | | | | 1651.91 | 1651.61 | 0.30 | 410-424 | | |
| | | | | 2901.67 | 2901.19 | 0.48 | 41-66 | | |
| | | | | 3408.94 | 3407.77 | 1.17 | 290-318 | | |

FIG. 16C

Identification of Proteins by Mass Spectrometry of Tryptic Fragments from ID Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 11 | 5 peaks match with BMP-3 | human | 4557371 (NCBI) | 1113.23 | 1113.31 | -0.08 | 361-368 | 48 | % coverage calculation is relative to the mature BMP-3, 183 AAS (290-472) |
|  |  |  |  | 1651.73 | 1651.91 | -0.18 | 410-424 |  |  |
|  |  |  |  | 1793.58 | 1794.02 | -0.44 | 346-360 |  |  |
|  |  |  |  | 2424.24 | 2424.81 | -0.57 | 373-392 |  |  |
|  |  |  |  | 3408.34 | 3407.77 | 0.57 | 290-318 |  |  |
|  | 5 peaks match with ribosome L6 | human | Q02878 (Swiss-Prot) | 1140.38 | 1140.23 | 0.15 | 114-122 | 16 |  |
|  |  |  |  | 1526.88 | 1526.86 | 0.02 | 141-155 |  |  |
|  |  | mouse | P47911 (Swiss-Prot) | 1059.15 | 1059.12 | 0.03 | 10-20 |  |  |
|  |  |  |  | 1145.36 | 1145.35 | 0.01 | 262-271 |  |  |
|  |  |  |  | 1386.74 | 1386.68 | 0.06 | 260-271 |  |  |
|  | 4 peaks match with TGF-β2 | human | P08112 (Swiss-Prot) | 1101.20 | 1101.26 | -0.06 | 303-311 | 52 |  |
|  |  |  |  | 1175.26 | 1175.42 | -0.16 | 400-409 |  |  |
|  |  |  |  | 2240.37 | 2240.60 | -0.23 | 312-328 |  |  |
|  |  |  |  | 2691.70 | 2691.91 | -0.21 | 340-362 |  |  |
| 18 | 5 peaks match with SPP24 | bovine | Q27967 (Swiss-Prot) | 1410.93 | 1411.60 | -0.67 | 42-53 | 30 |  |
|  |  |  |  | 1447.59 | 1447.65 | -0.06 | 113-124 |  |  |
|  |  |  |  | 1540.64 | 1540.60 | 0.04 | 86-98 |  |  |
|  |  |  |  | 1869.10 | 1869.05 | 0.05 | 62-77 |  |  |
|  |  |  |  | 2268.47 | 2268.57 | -0.10 | 33-53 |  |  |

FIG. 16D

Identification of Proteins by Mass Spectrometry of Tryptic Fragments from ID Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 22 | 5 peaks match with TGF-β2 | human | P08112 (Swiss-Prot) | 1101.15 | 1101.26 | -0.11 | 303-311 | 63 | |
| | | | | 1175.13 | 1175.42 | -0.29 | 400-409 | | |
| | | | | 2084.16 | 2084.42 | -0.26 | 312-347 | | |
| | | | | 2240.25 | 2240.60 | -0.35 | 312-328 | | |
| | | | | 2691.61 | 2691.91 | -0.30 | 340-362 | | |
| | 2 peaks match with SPP24 | bovine | Q27967 (Swiss-Prot) | 1411.23 | 1411.60 | -0.37 | 42-53 | 11 | |
| | | | | 1447.40 | 1447.65 | -0.25 | 113-124 | | |
| 25 | 5 peaks match with histone H1.x | human | JC4928 (PIR) | 1208.46 | 1208.40 | 0.06 | 48-57 | 14 | |
| | | | | 1221.71 | 1222.35 | -0.64 | 107-118 | | |
| | | | | 1349.85 | 1350.52 | -0.67 | 107-119 | | |
| | | | | 1364.57 | 1364.59 | -0.02 | 48-58 | | |
| | | | | 1732.23 | 1732.97 | -0.74 | 43-57 | | |
| | 5 peaks match with BMP-3 | human | 4557371 (NCBI) | 1060.43 | 1060.20 | 0.23 | 102-111 | 31 | % coverage calculation is relative to the mature BMP-3, 183 AAs (280-472) |
| | | | | 1438.83 | 1438.58 | 0.25 | 346-357 | | |
| | | | | 1566.92 | 1566.76 | 0.16 | 345-357 | | |
| | | | | 1651.80 | 1651.91 | -0.11 | 410-424 | | |
| | | | | 3408.86 | 3407.77 | 1.09 | 290-318 | | |

FIG. 16E

Identification of Proteins by Mass Spectrometry of Tryptic Fragments from ID Gels

| Band | Mass Spec Profile | Species | Accession Number | Mass Spec Data | Mass Spec Database | Mass Difference | AAs | % Coverage | Comments |
|---|---|---|---|---|---|---|---|---|---|
| 29 | 4 peaks match with human BMP-3 | human | 4557371 (NCBI) | 1113.22 | 1113.31 | -0.09 | 361-368 | 27 | % coverage calculation is relative to the mature BMP-3, 183 AAS (290-472) |
| | | | | 1438.70 | 1438.58 | 0.12 | 346-357 | | |
| | | | | 1566.86 | 1566.75 | 0.11 | 345-357 | | |
| | | | | 3409.04 | 3407.77 | 1.27 | 290-318 | | |

FIG. 16F

Quantitation of Identified BP proteins

| Identified protein | Percentage of Total Protein |
|---|---|
| LORP | 2 |
| BMP-3 | 11 |
| BMP-3 and A2-MG | 3 |
| RL6 & BMP-3 | 4 |
| Histone | 3 |
| Histone | 3 |
| Histone & BMP-3 | 4 |
| BMP-3 | 8 |
| RL32 & BMP-3 | 8 |
| RS2D | 5 |
| SPP24 & TGF-$\beta$2 | 6 |
| Total | 58% |

FIG. 18

Identification of Proteins by Mass Spectrometry of Fragments from 2D Gels

| Spot | Digest | Mass Spec Profile | Species | Acc. No. | MS Peaks Data | MS Peaks Database | Diff | AAs | % Coverage | Comments |
|---|---|---|---|---|---|---|---|---|---|---|
| 1 | Lys-C | 2 peaks match with Coagulation Factor XIIIb | Human | P05160 (Swiss-Prot) | 1837.01 | 1637.14 | -0.13 | 472-437 | 5 | |
| 2 | Trypsin | 2 peaks match with LORP | Human | NP002309 (Swiss-Prot) | 1921.85 | 1921.14 | 0.51 | 368-982 | 5 | peptide match confirmed by sequence analysis |
| | | | | | 2679.51 | N/A | N/A | 489-504 | | |
| 3 | Lys-C | 5 peaks match with Cathepsin L Precursor | Bovine | P25075 (Swiss-Prot) | 1609.57 | 1609.68 | -0.31 | 241-253 | 41 | |
| | | | | | 2410.89 | 2410.63 | 0.28 | 445-669 | | |
| | | | | | 1407.26 | 1406.60 | 9.40 | 105-118 | | |
| | | | | | 1546.64 | 1548.70 | 0.14 | 58-70 | | |
| | | | | | 1681.18 | 1660.80 | 0.36 | 21-33 | | |
| | | | | | 1881.46 | 1680.80 | -1.06 | 301-314 | | |
| | | | | | 1834.71 | 1634.00 | 0.71 | 318-334 | | |
| | | | | | 2352.90 | 2351.50 | 1.40 | 274-295 | | |
| | | | | | 2381.50 | 2380.70 | 12.50 | 239-251 | | |
| | | | | | 2721.51 | 2721.10 | 12.41 | 131-154 | | |

FIG. 19A

Identifications of Proteins by Mass Spectrometry of Fragments from 2D Gels

| Spot | Digest | Mass Spec Profile | Species | Acc. No. | MS Peaks | | | AAs | % Coverage | Comments |
|---|---|---|---|---|---|---|---|---|---|---|
| | | | | | Data | Database | Diff | | | |
| 7 | Lys-C | 4 peaks match with TGF-β2 | Bovine | P21214 (Swiss-Prot) | 774.56 | 774.80 | -0.34 | 26.31 | 42 | |
| | | | | | 809.69 | 809.94 | -0.25 | 32.37 | | |
| | | | | | 1175.12 | 1175.43 | -0.31 | 88.107 | | |
| | | | | | 3168.10 | 3166.66 | 1.44 | 1-25 | | |
| | Trypsin | 1 peak matches with SPP24 | Bovine | Q27957 (Swiss-Prot) | 2167.77 | 2167.51 | 0.26 | 42.60 | 10 | |
| 8 | Trypsin | 12 peaks match with Ribosome L3 | Bovine | P38872 (Swiss-Prot) | 917.39 | 917.14 | 0.25 | 348.355 | 37 | |
| | | | | | 984.23 | 984.15 | 0.08 | 10.18 | | |
| | | | | | 1193.62 | 1192.40 | 0.22 | 286-296 | | |
| | | | | | 1360.67 | 1360.65 | 0.02 | 249-250 | | |
| | | | | | 1484.60 | 1484.63 | 0.17 | 103-114 | | |
| | | | | | 1620.88 | 1620.82 | 0.04 | 103-115 | | |
| | | | | | 1778.64 | 1777.00 | -0.16 | 34-49 | | |
| | | | | | 2238.43 | 2238.55 | -0.12 | 30-49 | | |
| | | | | | 2325.99 | 2325.65 | 0.34 | 177-197 | | |
| | | | | | 2681.31 | 2681.04 | 0.27 | 200-223 | | |
| | | | | | 2597.94 | 2597.43 | -0.49 | 70-98 | | |
| | | | | | 2946.10 | 2946.35 | -0.25 | 198-223 | | |

FIG. 19B

Identification of Proteins by Mass Spectrometry of Fragments from 2D Gels

| Spot | Digest | Mass Spec Profile | Species | Acc. No. | MS Peaks Data | MS Peaks Database | Diff | AAs | % Coverage | Comments |
|---|---|---|---|---|---|---|---|---|---|---|
| 7 | Lys-C | 4 peaks match with TGF-β2 | Bovine | P21214 (Swiss-Prot) | 774.56 | 774.80 | -0.34 | 26.31 | 42 | |
| | | | | | 809.69 | 809.94 | -0.25 | 32-37 | | |
| | | | | | 1175.12 | 1175.43 | -0.31 | 88-107 | | |
| | | | | | 3168.10 | 3166.66 | 1.44 | 1-25 | | |
| | | 1 peak matches with SPP24 | Bovine | Q27957 (Swiss-Prot) | 2167.77 | 2167.51 | 0.26 | 42-60 | 10 | |
| 8 | Trypsin | 12 peaks match with Ribosome L3 | Bovine | P38872 (Swiss-Prot) | 917.39 | 917.14 | 0.25 | 348-355 | 37 | |
| | | | | | 984.23 | 984.15 | 0.08 | 10-18 | | |
| | | | | | 1192.62 | 1192.40 | 0.22 | 286-296 | | |
| | | | | | 1360.67 | 1360.65 | 0.02 | 249-250 | | |
| | | | | | 1484.60 | 1484.63 | 0.17 | 103-114 | | |
| | | | | | 1620.88 | 1620.82 | 0.04 | 103-115 | | |
| | | | | | 1778.64 | 1777.00 | -0.16 | 34-49 | | |
| | | | | | 2238.43 | 2238.55 | -0.12 | 30-49 | | |
| | | | | | 2325.99 | 2325.65 | 0.34 | 177-197 | | |
| | | | | | 2681.31 | 2681.04 | 0.27 | 200-223 | | |
| | | | | | 2597.94 | 2597.43 | -0.49 | 70-98 | | |
| | | | | | 2946.10 | 2946.35 | -0.25 | 198-223 | | |

FIG. 19C

Identification of Proteins by Mass Spectrometry of Fragments from 2D Gels

| Spot | Digest | Mass Spec Profile | Species | Acc. No. | MS Peaks Data | MS Peaks Database | Diff | AAs | % Coverage | Comments |
|---|---|---|---|---|---|---|---|---|---|---|
| 9 | Trypsin | 7 peaks match with Ribosome S3 | Mouse | P97351 (Swiss-Prot) | 920.05 | 820.10 | -0.05 | 19-25 | 29 | |
| | | | | | 1218.29 | 1218.31 | -0.02 | 152-181 | | |
| | | | | | 1346.82 | 1348.49 | 0.13 | 151-161 | | |
| | | | | | 1516.69 | 1516.69 | 0.00 | 174-186 | | |
| | | | | | 1593.72 | 1593.82 | -0.10 | 94-108 | | |
| | | | | | 1719.91 | 1720.08 | -0.09 | 199-212 | | |
| | | | | | 1953.12 | 1953.16 | -0.04 | 65-81 | | |
| 10 | Trypsin | 4 peaks match with histone H1.c | Human | 07658 (NCBI) | 1327.75 | 1327.58 | 0.19 | 34-46 | 23 | |
| | | | | | 1579.70 | 1579.71 | -0.01 | 65-78 | | |
| | | | | | 1707.65 | 1707.89 | -0.24 | 64-79 | | |
| | | | | | 2147.17 | 2147.53 | -0.36 | 1-21 | | |
| 11 | Trypsin | 6 peaks match with Ribosome S4 | Human | P12750 (Swiss-Prot) | 1188.48 | 1168.38 | 0.10 | 230-239 | 23 | |
| | | | | | 1216.39 | 1216.39 | 0.00 | 134-144 | | |
| | | | | | 1354.09 | 1353.61 | 0.42 | 230-241 | | |
| | | | | | 1507.81 | 1507.89 | 0.12 | 108-210 | | |
| | | | | | 1557.75 | 1557.98 | -0.23 | 37-48 | | |
| | | | | | 2140.34 | 2140.58 | -0.24 | 221-239 | | |
| | | | | | 2591.80 | 2591.90 | -0.10 | 77-98 | | |

FIG. 19D

Quail Chorioallantoic Membrane (CAM) Angiogenesis Assay

Quail Chorioallantoic Membrane (CAM) Angiogenesis Assay

Quail Chorioallantoic Membrane (CAM) Angiogenesis Assay

Black and white images of CAM vasculature after growth factor treatment

PBS
100 %

10 μg/ml bFGF
145 %

10 μg/ml BP
224 %

10 μg/ml IBP
186 %

SEQUENCE LISTING

```
<160> NUMBER OF SEQ ID NOS: 31

<210> SEQ ID NO 1
<211> LENGTH: 11
<212> TYPE: PRT
<213> ORGANISM: Bos Taurus
<220> FEATURE:
<221> NAME/KEY: MISC_FEATURE
<222> LOCATION: (1)..(1)
<223> OTHER INFORMATION: Xaa = any amino acid

<400> SEQUENCE: 1

Xaa Leu Ala Ala Ala Gly Tyr Asp Val Glu Lys
1               5                   10

<210> SEQ ID NO 2
<211> LENGTH: 11
<212> TYPE: PRT
<213> ORGANISM: Bos Taurus

<400> SEQUENCE: 2

Ala Leu Ala Ala Ala Gly Tyr Asp Val Glu Lys
1               5                   10

<210> SEQ ID NO 3
<211> LENGTH: 11
<212> TYPE: PRT
<213> ORGANISM: Bos Taurus

<400> SEQUENCE: 3

Ser Leu Glu Lys Val Cys Ala Asp Leu Ile Arg
1               5                   10

<210> SEQ ID NO 4
<211> LENGTH: 14
<212> TYPE: PRT
<213> ORGANISM: Bos Taurus

<400> SEQUENCE: 4

Val Val Cys Gly Met Leu Gly Phe Pro Ser Glu Ala Pro Val
1               5                   10

<210> SEQ ID NO 5
<211> LENGTH: 14
<212> TYPE: PRT
<213> ORGANISM: Bos Taurus

<400> SEQUENCE: 5

Val Val Cys Gly Met Leu Gly Phe Pro Gly Glu Lys Arg Val
1               5                   10
```

```
<210> SEQ ID NO 6
<211> LENGTH: 15
<212> TYPE: PRT
<213> ORGANISM: Bos Taurus

<400> SEQUENCE: 6

Ser Thr Gly Val Leu Leu Pro Leu Gln Asn Asn Glu Leu Pro Gly
1               5                   10                  15

<210> SEQ ID NO 7
<211> LENGTH: 20
<212> TYPE: PRT
<213> ORGANISM: Bos Taurus

<400> SEQUENCE: 7

Ser Thr Gly Val Leu Leu Pro Leu Gln Asn Asn Glu Leu Pro Gly Ala
1               5                   10                  15

Glu Tyr Gln Tyr
            20

<210> SEQ ID NO 8
<211> LENGTH: 9
<212> TYPE: PRT
<213> ORGANISM: Bos Taurus

<400> SEQUENCE: 8

Ser Thr Gly Val Leu Leu Pro Leu Gln
1               5

<210> SEQ ID NO 9
<211> LENGTH: 8
<212> TYPE: PRT
<213> ORGANISM: Bos Taurus
<220> FEATURE:
<221> NAME/KEY: MISC_FEATURE
<222> LOCATION: (7)..(7)
<223> OTHER INFORMATION: Xaa = any amino acid

<400> SEQUENCE: 9

Ser Gln Thr Leu Gln Phe Xaa Glu
1               5

<210> SEQ ID NO 10
<211> LENGTH: 8
<212> TYPE: PRT
<213> ORGANISM: Bos Taurus

<400> SEQUENCE: 10

Ser Gln Thr Leu Gln Phe Asp Glu
1               5

<210> SEQ ID NO 11
<211> LENGTH: 4
<212> TYPE: PRT
<213> ORGANISM: Bos Taurus

<400> SEQUENCE: 11

Val Tyr Ala Phe
1

<210> SEQ ID NO 12
<211> LENGTH: 14
<212> TYPE: PRT
<213> ORGANISM: Bos Taurus
```

-continued

```
<400> SEQUENCE: 12

His Ala Gly Lys Tyr Ser Arg Glu Lys Asn Thr Pro Ala Pro
1               5                   10

<210> SEQ ID NO 13
<211> LENGTH: 14
<212> TYPE: PRT
<213> ORGANISM: Bos Taurus

<400> SEQUENCE: 13

His Gly Gly Lys Tyr Ser Arg Glu Lys Asn Gln Pro Lys Pro
1               5                   10

<210> SEQ ID NO 14
<211> LENGTH: 9
<212> TYPE: PRT
<213> ORGANISM: Bos Taurus

<400> SEQUENCE: 14

Ser Gln Thr Leu Gln Phe Asp Glu Gln
1               5

<210> SEQ ID NO 15
<211> LENGTH: 8
<212> TYPE: PRT
<213> ORGANISM: Bos Taurus

<400> SEQUENCE: 15

Ser Leu Lys Pro Ser Asn His Ala
1               5

<210> SEQ ID NO 16
<211> LENGTH: 9
<212> TYPE: PRT
<213> ORGANISM: Bos Taurus

<400> SEQUENCE: 16

Ala Ala Leu Arg Pro Leu Val Lys Pro
1               5

<210> SEQ ID NO 17
<211> LENGTH: 9
<212> TYPE: PRT
<213> ORGANISM: Bos Taurus

<400> SEQUENCE: 17

Ala His Ile Gln Val Glu Arg Tyr Val
1               5

<210> SEQ ID NO 18
<211> LENGTH: 5
<212> TYPE: PRT
<213> ORGANISM: Bos Taurus

<400> SEQUENCE: 18

Ala Ile Val Glu Arg
1               5

<210> SEQ ID NO 19
<211> LENGTH: 7
<212> TYPE: PRT
<213> ORGANISM: Bos Taurus

<400> SEQUENCE: 19
```

```
His Gln Ser Asp Arg Tyr Val
1               5
```

```
<210> SEQ ID NO 20
<211> LENGTH: 15
<212> TYPE: PRT
<213> ORGANISM: Bos Taurus
<220> FEATURE:
<221> NAME/KEY: MISC_FEATURE
<222> LOCATION: (1)..(10)
<223> OTHER INFORMATION: Xaa = any amino acid

<400> SEQUENCE: 20

Xaa Ala Leu Phe Gly Ala Gln Leu Gly Xaa Ala Leu Gly Pro Ile
1               5                   10                  15

<210> SEQ ID NO 21
<211> LENGTH: 10
<212> TYPE: PRT
<213> ORGANISM: Bos Taurus

<400> SEQUENCE: 21

Ser Gln Thr Leu Gln Phe Asp Glu Gln Thr
1               5                   10

<210> SEQ ID NO 22
<211> LENGTH: 6
<212> TYPE: PRT
<213> ORGANISM: Bos Taurus
<220> FEATURE:
<221> NAME/KEY: MISC_FEATURE
<222> LOCATION: (5)..(5)
<223> OTHER INFORMATION: Xaa = any amino acid

<400> SEQUENCE: 22

Ser Gln Thr Leu Xaa Phe
1               5

<210> SEQ ID NO 23
<211> LENGTH: 6
<212> TYPE: PRT
<213> ORGANISM: Bos Taurus

<400> SEQUENCE: 23

Ser Gln Thr Leu Gln Phe
1               5

<210> SEQ ID NO 24
<211> LENGTH: 13
<212> TYPE: PRT
<213> ORGANISM: Bos Taurus

<400> SEQUENCE: 24

Val Leu Ala Thr Val Thr Lys Pro Val Gly Gly Asp Lys
1               5                   10

<210> SEQ ID NO 25
<211> LENGTH: 4
<212> TYPE: PRT
<213> ORGANISM: Bos Taurus

<400> SEQUENCE: 25

Val Phe Ala Leu
1

<210> SEQ ID NO 26
```

```
-continued

<211> LENGTH: 10
<212> TYPE: PRT
<213> ORGANISM: Bos Taurus

<400> SEQUENCE: 26

Ala Val Pro Gln Leu Gln Gly Tyr Leu Arg
1               5                   10

<210> SEQ ID NO 27
<211> LENGTH: 10
<212> TYPE: PRT
<213> ORGANISM: Bos Taurus

<400> SEQUENCE: 27

Ala Ile Pro Gln Leu Gln Gly Tyr Leu Arg
1               5                   10

<210> SEQ ID NO 28
<211> LENGTH: 9
<212> TYPE: PRT
<213> ORGANISM: Bos Taurus

<400> SEQUENCE: 28

Ala Leu Asp Ala Ala Tyr Cys Phe Arg
1               5

<210> SEQ ID NO 29
<211> LENGTH: 14
<212> TYPE: PRT
<213> ORGANISM: Bos Taurus

<400> SEQUENCE: 29

Gly Tyr Asn Ala Asn Phe Cys Ala Gly Ala Cys Pro Tyr Leu
1               5                   10

<210> SEQ ID NO 30
<211> LENGTH: 9
<212> TYPE: PRT
<213> ORGANISM: Bos Taurus

<400> SEQUENCE: 30

Val Asn Ser Gln Ser Leu Ser Pro Tyr
1               5

<210> SEQ ID NO 31
<211> LENGTH: 8
<212> TYPE: PRT
<213> ORGANISM: Bos Taurus

<400> SEQUENCE: 31

Lys Ala Ala Lys Pro Ser Val Pro
1               5
```

METHOD OF PROMOTING NATURAL BYPASS

CROSS-REFERENCE TO RELATED APPLICATIONS

This application is a continuation-in-part of U.S. Ser. No. 09/173,989, filed Oct. 16, 1998, now U.S. Pat. No. 6,211,157, and entitled "Protein Mixtures to Induce Therapeutic Angiogenesis," which is incorporated herein by reference.

STATEMENT REGARDING FEDERALLY SPONSORED RESEARCH OR DEVELOPMENT

Not applicable.

FIELD OF THE INVENTION

The present invention relates to a method for inducing the growth of blood vessels in instances where it is desirable to increase the supply of blood to a portion of a living body. More particularly, the present invention comprises a novel angiogenic factor. Still more particularly, the present invention relates to the use of mixtures of protein extracted from bone to cause a natural vascular bypass effect.

BACKGROUND OF THE INVENTION

There are many medical circumstances in which an increase in the supply of blood to living tissue is indicated. These include: burns and wound healing, in which the incorporation of angiogenic factors into artificial skin may facilitate the formation of blood vessels in the healing wound and reduce the risk of infection; cardiovascular disease, in which repair of anginal or ischemic cardiac tissue can be effected by causing the ingrowth of new blood vessels; stroke, where increased blood supply to the brain can reduce the risk of transient ischemic attack and/or cerebral arterial deficiency; and peripheral vascular disease, in which blood flow in the extremities is diminished. In each case, it is believed that the growth of new blood vessels will increase the volume of blood circulating through the tissue in question, and correspondingly increase the amount of oxygen and nutrients available to that tissue.

One common cause of decreased blood flow is atherosclerosis. Atherosclerosis affects the blood vessels, including those of the heart, and is a major cause of cardiovascular disease, stroke and peripheral vascular disease. This disease may have its beginnings early in life and is first noted as a thickening of the arterial walls. This thickening is an accumulation of fat, fibrin, cellular debris and calcium. The resultant narrowing of the lumen of the afflicted vessel is called stenosis. Stenosis impedes and reduces blood flow. Hypertension and dysfunction of the organ or area of the body that suffers the impaired blood flow can result. As the buildup on the inner wall of a vessel thickens, the vessel wall loses the ability to expand and contract. Also, the vessel loses its viability and becomes weakened and susceptible to bulging, also known as aneurysm. In the presence of hypertension or elevated blood pressure, aneurysms will frequently dissect and ultimately rupture.

Small vessels, such as the arteries that supply blood to the heart, legs, intestines and other areas of the body, are particularly susceptible to atherosclerotic narrowing. When an artery in the leg or intestine is affected, the resultant loss of blood supply to the leg or segment of the intestine may result in gangrene. Atherosclerotic narrowing of one or more of the coronary arteries limits and in some instances prevents blood flow to portions of the heart muscle. Depending upon the severity of the occlusion and its location within the coronary circulation system, pain, cardiac dysfunction or death may result. Because the consequences of blocked arteries are so serious, reliable treatments are highly desirable.

In many instances, it is possible to correct aneurysms and stenosis of major arteries using plastic reconstruction that does not require any synthetic graft or patch materials. In other instances, such as where the disease is extensive and the vessel is no longer reliable, the blocked or weakened portion of the vessel is usually replaced with a graft. In such case, the affected vessel section is transected and removed and a synthetic patch, conduit or graft is sewn into its place. These types of procedures, including coronary artery bypass grafting (CABG) and percutaneous transluminal coronary angioplasty (PTCA), are routinely performed for the purpose of alleviating ischemia.

Nevertheless, coronary artery disease alone is responsible for approximately 550,000 deaths each year in the United States. Peripheral vascular disease results in lower limb amputation in about 150,000 patients each year, with a subsequent mortality rate of 40% within two years of amputation. Some of the difficulty in treating arterial occlusion may lie in the fact that each of these surgical procedures is associated with a certain incidence of restenosis and may not be appropriate in certain instances. This is particularly true when the patient is elderly or has undergone a previous CABG or PTCA procedure. Furthermore, in such cases, a less invasive technique would be preferred. In particular, it would be advantageous to be able to stimulate the surrounding tissue to produce for itself new vessels that would compensate for the occluded vessels.

While angiogenic, or "vessel-growing," factors in general have been the subject of much research, no angiogenic factor has yet been found to be effective for promoting the desired natural bypass effect. Examples of such growth factors are transforming growth factor beta (TGF-$\beta$), osteonectin or SPARC, platelet-derived growth factor (PDGF), basic fibroblast growth factor (bFGF) and vascular endothelial growth factor (VEGF). All of these growth factors are either synthetic, meaning they are manufactured chemically from non-living sources, or are produced by recombinant manufacturing processes. Each of these angiogenic factors comprises only a single protein and possesses only a single functionality. In addition, many of the known angiogenic compounds are exceedingly difficult and/or expensive to manufacture.

Hence, it is desired to provide an effective angiogenic factor that is easy to manufacture from readily available materials, easily administered by the surgeon and effective at stimulating the growth of new blood vessels into the treated tissue.

BRIEF SUMMARY OF THE INVENTION

The present invention comprises an angiogenic factor that is easily manufactured from readily available materials, easily administered by the surgeon and effective at stimulating the growth of new blood vessels into the treated tissue. The angiogenic factor of the present invention comprises a group of proteins extracted from bone. It has been found that the mixtures of proteins produced by certain processes are particularly effective angiogenic agents. These angiogenic agents can be administered as part of the treatment of an existing vascular disorder, or can play a role in early intervention and prevention if administered in certain cases. In particular, the present angiogenic agents can be introduced into tissue in the vicinity of an occluded vessel so as to cause the formation of new vessels that bypass the occluded vessel. In this manner, a natural bypass mechanism is provided.

The angiogenic mixtures of bone proteins used according to the present invention are produced by a multi-step process that includes at least one ultrafiltration step, an anion exchange chromatography step, a cation exchange chromatography step and a high performance liquid chromatography (HPLC) purification step.

In particularly preferred embodiments, the invention provides a method for promoting natural bypass in a mammal so provide increased blood flow to tissue served by an occluded or partly occluded vessel, a method for promoting vessel growth to heal a heart artery that has been blocked, or a method for promoting angiogenesis to assist in recovery from tissue damage.

In each instance, the method preferably comprises administering to the mammal a mixture of proteins derived from ground bone. The mixture of proteins preferably comprises at least two growth factors selected from the group consisting of bone morphogenic protein-2 (BMP-2), bone morphogenic protein-3 (BMP-3), bone morphogenic protein-4 (BMP-4), bone morphogenic protein-5 (BMP-5), bone morphogenic protein-6 (BMP-6), bone morphogenic protein-7 (BMP-7), transforming growth factor β1 (TGF-β1), transforming growth factor β2 (TGF-β2), transforming growth factor β3 (TGF-β3), and fibroblast growth factor 1 (FGF-1).

The mammal to which the present method is applied can be a human, and the mixture can be administered subcutaneously, intramuscularly, or intravenously. The bone-derived protein mixture may be derived from bovine bone. The mixture can be administered discretely or continuously.

In a preferred embodiment, the mixture further comprises a growth factor selected from insulin-like growth factor-1 (IGF-1), epidermal growth factor (EGF), hepatocyte growth factor (HGF), transforming growth factor α(TGF-α), or platelet-derived growth factor (PDGF), and optionally includes a preservative or an adjuvant. Particularly preferred mixtures comprises BMP-2, BMP-3, BMP-7, TGF-β, and FGF, or the mixture derived by (i) grinding mammalian bone, to produce ground bone; (ii) cleaning the ground bone, to produce cleaned ground bone; (iii) demineralizing the cleaned ground bone, to produce demineralized cleaned ground bone; (iv) extracting protein from the demineralized cleaned ground bone using a protein denaturant; to yield extracted protein; (v) ultrafiltering the extracted protein to separate out high molecular weight proteins; (vi) ultrafiltering the extracted protein to separate out low molecular weight proteins; (vii) transferring the extracted protein to a non-ionic denaturant; (viii) subjecting the extracted protein to an anion exchange process; (ix) subjecting the extracted protein to a cation exchange process; and (x) subjecting the extracted protein to a reverse phase HPLC process.

BRIEF DESCRIPTION OF THE DRAWINGS

For a more detailed description of the present invention, reference will now be made to the accompanying Figures, wherein:

FIG. 9A indicates the presence of BMP-3 and BMP-2. FIG. 9B indicates the presence of BMP-3 and BMP-7. FIG. 9C indicates the presence of BMP-7 and BMP-2, and FIG. 12D indicates the presence of BMP-3 and TGF-β1;

FIG. 14 is a chart showing antibody listing and reactivity;

FIGS. 15A–B together comprise a chart showing tryptic fragment sequencing data for components of a protein mixture according to an embodiment of the present invention;

FIGS. 16A–F together comprise a chart showing tryptic fragment mass spectrometry data for components of a protein mixture according to an embodiment of the present invention;

FIG. 18 is a chart illustrating the relative mass, from scanning densitometer quantification, of protein components in a protein mixture according to an embodiment of the present invention;

FIGS. 19A–C together comprise a chart showing mass spectrometry data of various protein fragments from 2D gels of a protein mixture according to an embodiment of the present invention;

DETAILED DESCRIPTION OF THE PREFERRED EMBODIMENTS

Figure 1:
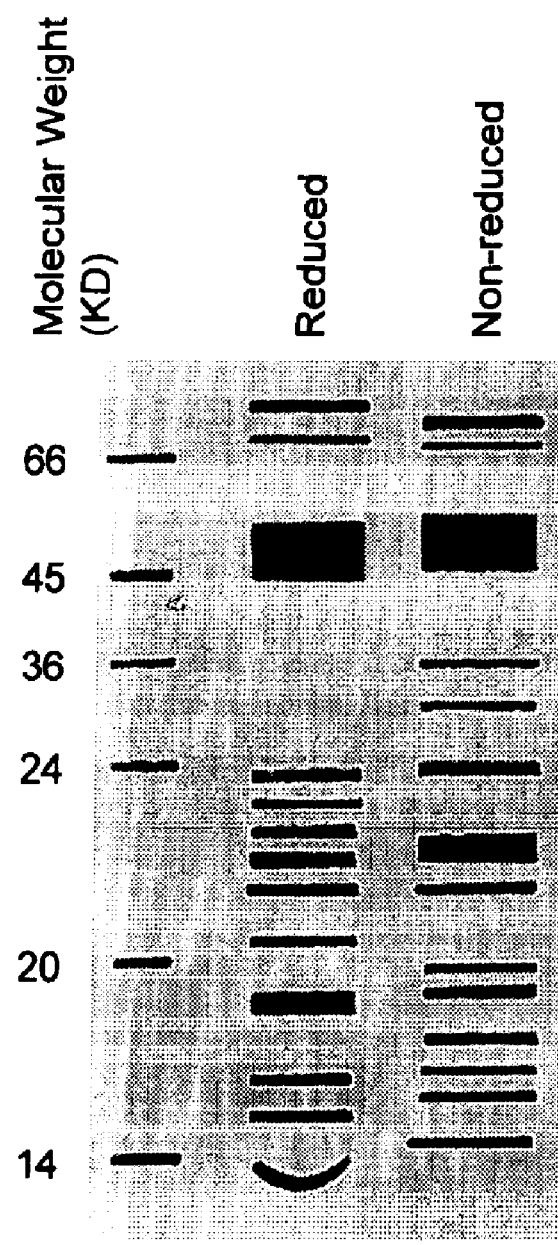
FIG. 1 illustrates an SDS-PAGE of one embodiment of the present angiogenic protein mixture, both in reduced and non-reduced forms.

Angiogenesis is a complex process involving several different cell types and molecular signaling events. Endothelial cells must secrete proteases to dissolve cell-cell and cell-matrix attachments, migrate and proliferate to form new vascular branches. Although single factors such as bFGF and VEGF have shown promise as angiogenic agents, it has been discovered that a more robust angiogenic response may be obtained through the use of an agent that comprises a mixture of proteins. This may be due in part to a synergistic effect of the combined proteins on the subject tissue. Thus, according to a preferred embodiment of the present invention, a natural bypass effect is achieved by injecting an angiogenic mixture of bone proteins into tissue in need of increased blood flow.

In one embodiment, a natural bypass effect is promoted by administering a mammal a mixture of growth factors derived from bone. In another embodiment, vessel growth is promoted so as to heal a heart artery that has been blocked. In still another embodiment, angiogenesis is promoted in ischemic tissue so as to assist in recovery.

The bone-derived angiogenic protein (BDAP) mixture preferred for use in the present invention is preferably administered directly to ischemic tissue in a suitable carrier. For example, in some instances, it may be desired to apply the angiogenic factor in a carrier that allows it to be absorbed quickly, while in other instances it may be desired to apply the angiogenic factor in a controlled, time-release manner. In other instances, a single dose or other variation may be preferred. In general, the preferred carrier material will vary depending on the desired clinical application or site of administration. Polylactic acid, polyglycolic acid and their copolymers, collagen, PLURONIC® (polyoxyalkylene ether co-polymer surfactant), and povidone (polyvinylpyrrolidone) are all examples of biocompatible materials that can be combined with BDAP mixtures to stimulate angiogenesis.

Characterization of Preferred Growth Factors

A preferred angiogenic mixture of bone proteins is produced by a multi-step process that includes an ultrafiltration step, an anion exchange chromatography step, a cation exchange chromatography step and a high performance liquid chromatography (HPLC) purification step as described in detail below. Preferred processes for producing the angiogenic protein mixtures of the present invention are described in full detail in U.S. Pat. Nos. 5,290,763 and 5,371,191, which are incorporated herein in their entireties. The processes can be summarized as follows. In a first step, demineralized bone particles from a suitable source (such as crushed bovine bone) are subjected to protein extraction using guanidine hydrochloride. The extract solution is filtered, and subjected to a two step ultrafiltration process. In the first ultrafiltration step, an ultrafiltration membrane having a nominal molecular weight cut off (MWCO) of 100 kD is preferably employed. The retentate is discarded and the filtrate is subjected to a second ultrafiltration step using an ultrafiltration membrane preferably having a nominal MWCO of about 10 kD. The retentate is then subjected to diafiltration to substitute urea for guanidine. The protein-containing urea solution is then subjected to sequential ion exchange chromatography, first anion exchange chromatography followed by cation exchange chromatography. For the anion exchange process, a strongly cationic resin is used, preferably having quaternary amine functional groups. Typically, the eluant for the anion exchange process has a conductivity from about 10,260 micromhos (μmhos) ($1.026 \times 10^{-2}$ siemens (S)) to about 11,200 μmhos ($1.120 \times 10^{-2}$ S). For the cation exchange process, a strongly anionic resin is used, preferably having sulfonic acid functional groups. The eluant for the cation exchange process typically has a conductivity from about 39,100 μmhos ($3.91 \times 10^{-2}$ S) to about 82,700 μmhos ($8.27 \times 10^{-2}$ S) or more.

In the process described above, the proteins are advantageously kept in solution. According to the present invention, the proteins produced by the above process are then subjected to HPLC. The HPLC process preferably utilizes a column containing hydrocarbon-modified silica packing material. The proteins can be loaded onto the HPLC column in a solution of aqueous trifluoracetic acid or other suitable solvent, such as heptafluorobutyric acid, hydrochloric or phosphoric acid. Preferably, a trifluoracetic acid solution having a concentration of from about 0.05 percent by volume to about 0.15 percent by volume, and more preferably about 0.1 percent by volume trifluoracetic acid is used.

Proteins are eluted from the HPLC column with an organic solvent/water mixture suitable for obtaining the desired proteins. A preferred eluant in the HPLC process is an acetonitrile solution. The preferred eluant typically has an acetonitrile concentration which varies, during elution, from about 30 percent by volume to about 45 percent by volume. In preferred embodiments, the acetonitrile concentration in the eluant is increased in increments of between about 0.30 percent by volume and about 0.40 percent by volume per minute until the desired highest concentration of acetonitrile is achieved. Proteins can be recovered from the HPLC process eluant by means generally known in the art. A preferred angiogenic fraction of the eluted proteins occurs when the acetonitrile concentration in the eluant is between about 33 percent by volume and about 37 percent by volume.

The purification processes described above yield novel angiogenic protein mixtures. Because they comprise mixtures of proteins, these angiogenic factors are most easily described in terms of their properties. Hence, in one embodiment of the present angiogenic factor, the factor is a mixture of a number of proteins having the sodium dodecyl sulfate polyacrylamide gel electrophoresis (SDS-PAGE) profile shown in FIG. 1.

Another characterization of the present invention is a mixture of proteins having a preferred amino acid composition of about 20–25 mole percent of acidic amino acids [ASP(+ASN) and GLU(+GLN)]; about 10–15 mole percent of hydroxy amino acids (SER and THR); about 35–45 mole percent aliphatic amino acids (ALA, GLY, PRO, MET, VAL, ILE, and LEU); about 4–10 mole percent aromatic amino acids (TYR and PHE); and about 10–20 mole percent basic amino acids (HIS, ARG and LYS). More particularly, this embodiment of the angiogenic protein mixture amino preferably has an amino acid composition of about 23.4 mole percent of acidic amino acids [ASP(+ASN) and GLU(+GLN)]; about 13.5 mole percent of hydroxy amino acids (SER and THR); about 40.0 mole percent aliphatic amino acids (ALA, GLY, PRO, MET, VAL, ILE, and LEU); about 6.8 mole percent aromatic amino acids (TYR and PHE); and about 16.6 mole percent basic amino acids (HIS, ARG and LYS). (TRP, CYS and ½ CYS were not measured and are not included in the calculation of mole percent.)

An alternative embodiment of the present angiogenic factor can be defined as a different fraction of the total protein stream exiting the HPLC process. More particularly, the proteins eluted when the eluant has an acetonitrile concentration of from about 37 to about 39.5 percent by volume have been found to have surprising angiogenic activity. The mixture defined in this manner contains hundreds of natural proteins. It is believed that the angiogenic activity of proteins obtained in this manner may be further enhanced by selecting smaller fractions of the eluant and quantitatively comparing the angiogenic activity of each fraction.

Figure 2:
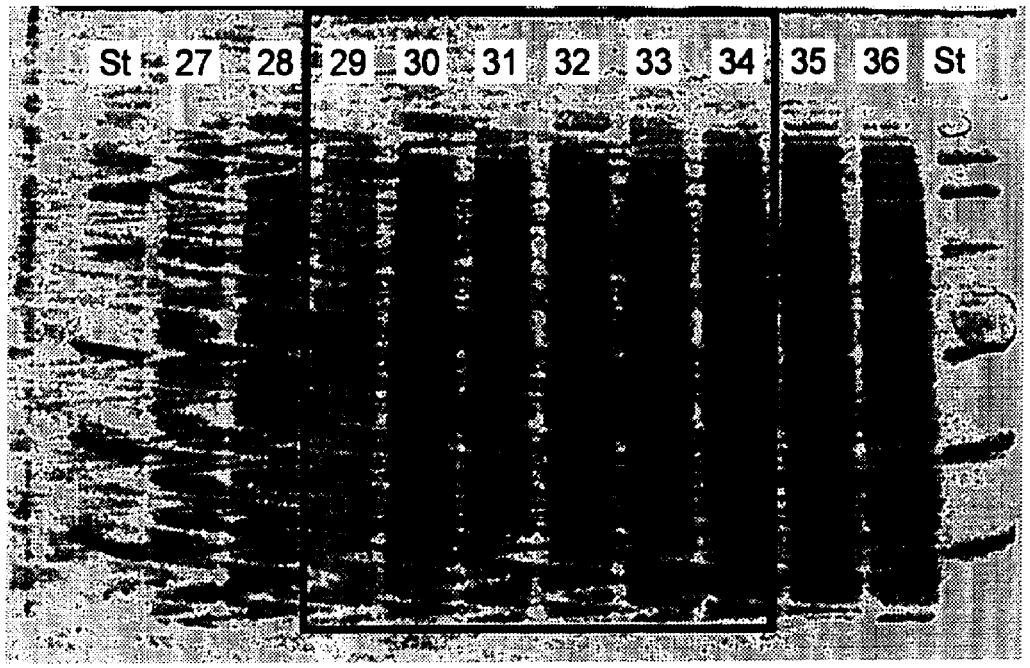
FIG. 2 is an SDS-PAGE gel of HPLC fractions 27–36 of a protein mixture according to an embodiment of the present invention.
Figure 3:
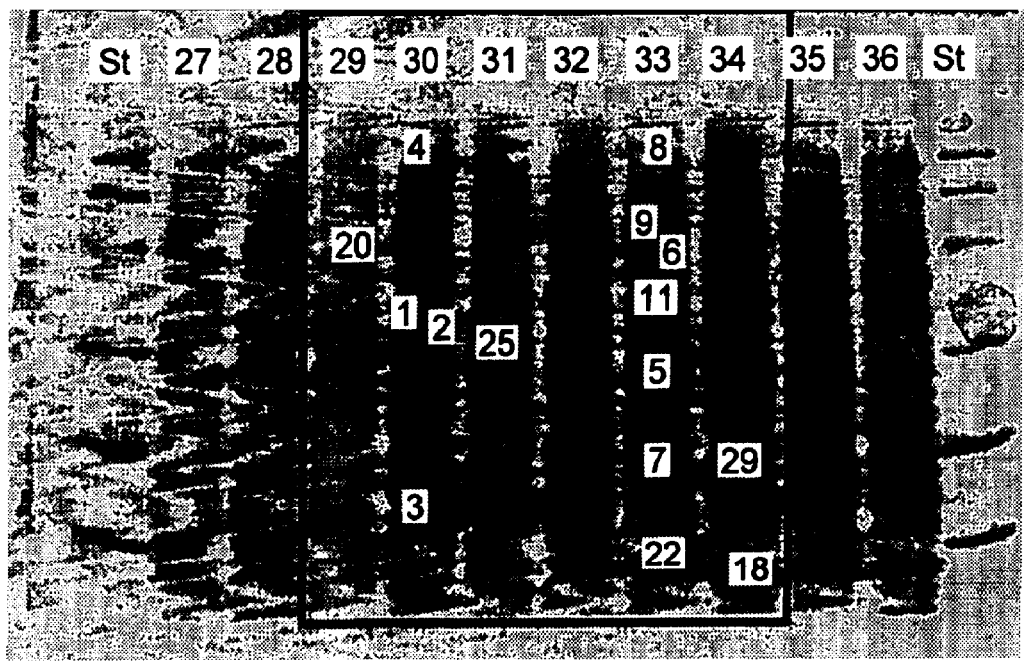
FIG. 3 is an SDS-PAGE gel with identified bands indicated according to the legend of FIG. 4.

In addition to the foregoing, BP has been partially characterized as follows: high performance liquid chromatography (HPLC) fractions have been denatured, reduced by DTT, and separated by sodium dodecyl sulfate polyacrylamide gel electrophoresis (SDS-PAGE). One minute HPLC fractions from 27 to 36 minutes are shown in FIG. 2. Size standards (ST) of 14, 21, 31, 45, 68 and 97 kDa were obtained as Low range size standards from BIORAD™ and are shown at either end of the coomassie blue stained gel. In the usual protocol, HPLC fractions 29 through 34 are pooled to produce BP (see boxes, FIGS. 2 and 3), as shown in a similarly prepared SDS-PAGE gel in FIG. 17B.

The various components of BP were characterized by mass spectrometry and amino acid sequencing of tryptic fragments where there were sufficient levels of protein for analysis. The major bands in the ID gel (as numerically identified in FIG. 3) were excised, eluted, subjected to tryptic digestion and the fragments were HPLC purified and sequenced. The sequence data was compared against known sequences, and the best matches are shown in FIGS. 12A–B. These identifications are somewhat tentative, in that only portions of the entire proteins have been sequenced and, in some cases, there is variation between the human and bovine analogs for a given protein.

Figure 4:
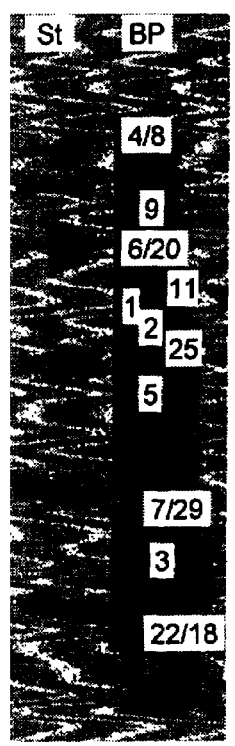
FIG. 4 is an SDS-PAGE gel of a protein mixture according to an embodiment of the present invention with identified bands indicated, as provided in the legend.
Figure 7A:
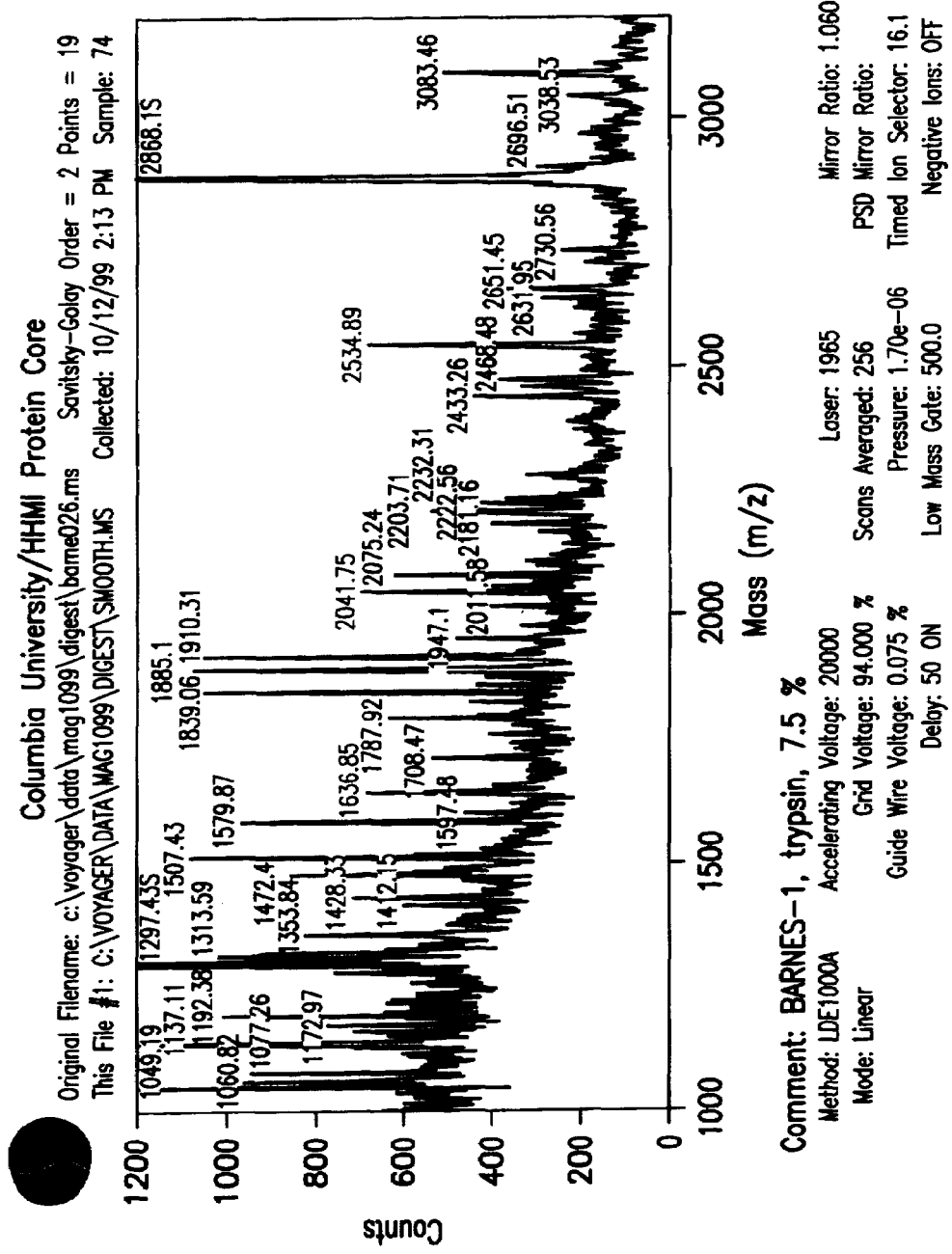
FIGS. 7A–O are mass spectrometer results for tryptic fragments from one dimensional (1-D) gels of a protein mixture according to an embodiment of the present invention.
Figure 7B:
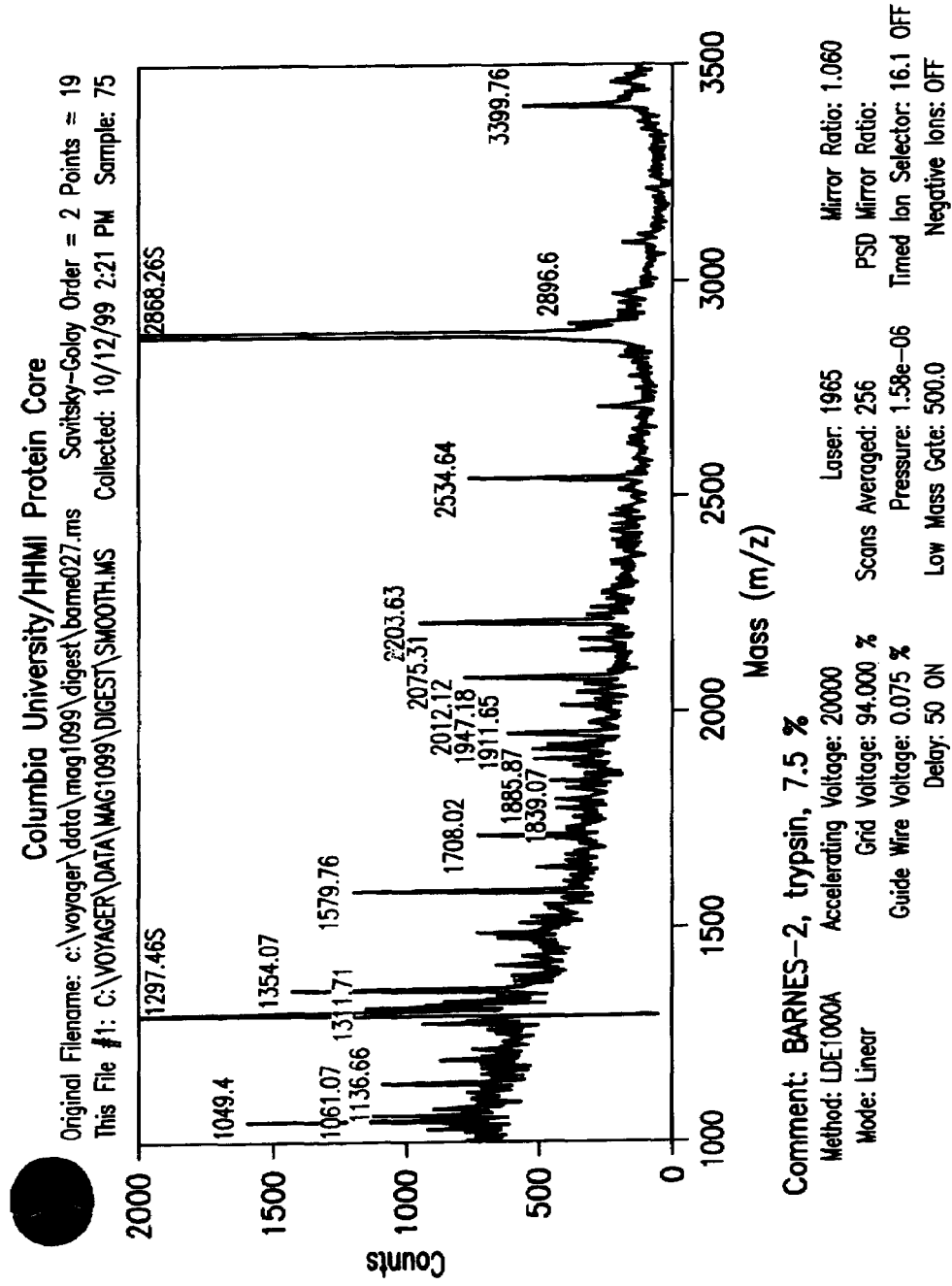
Figure 7C:
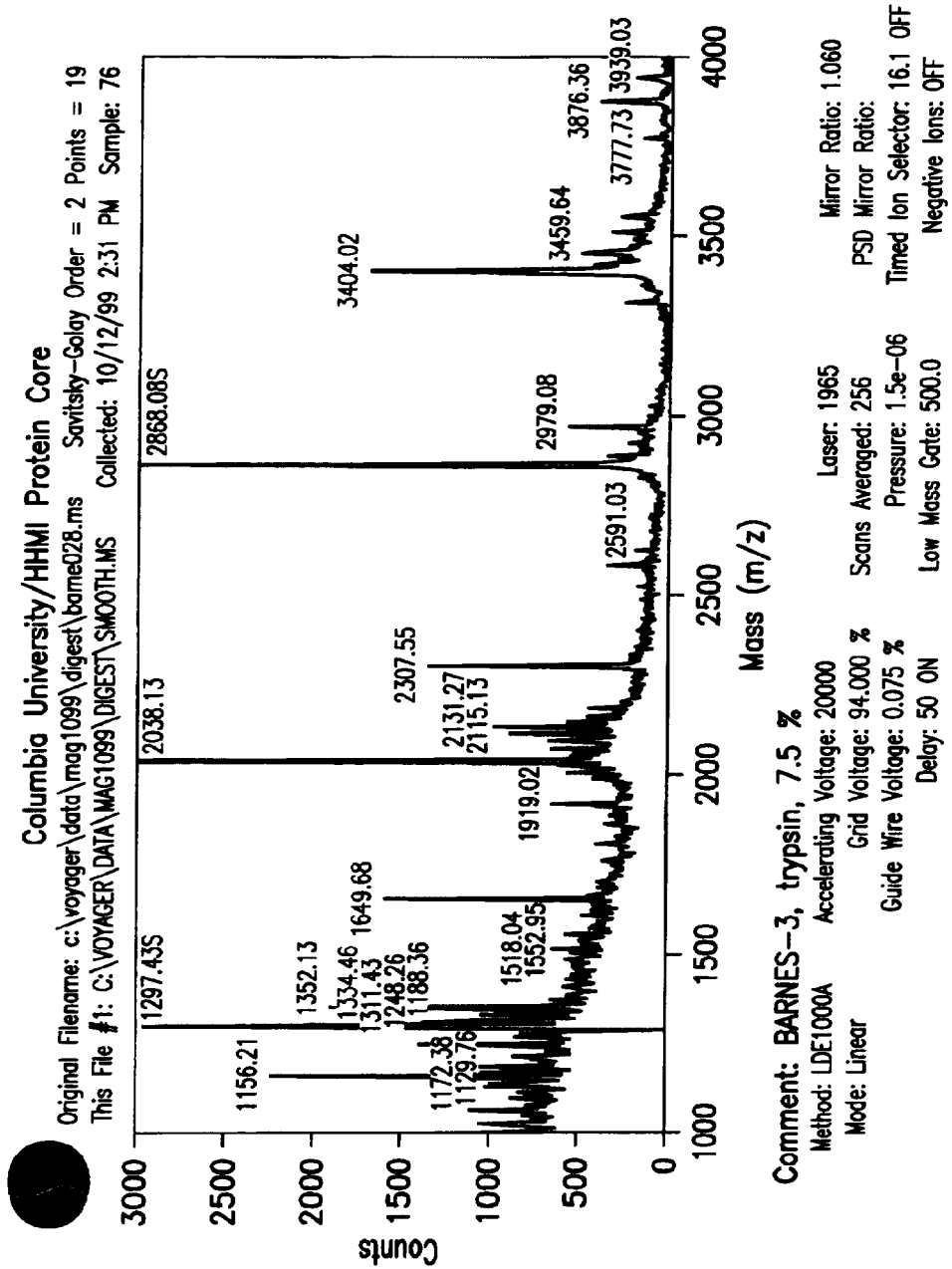
Figure 7D:
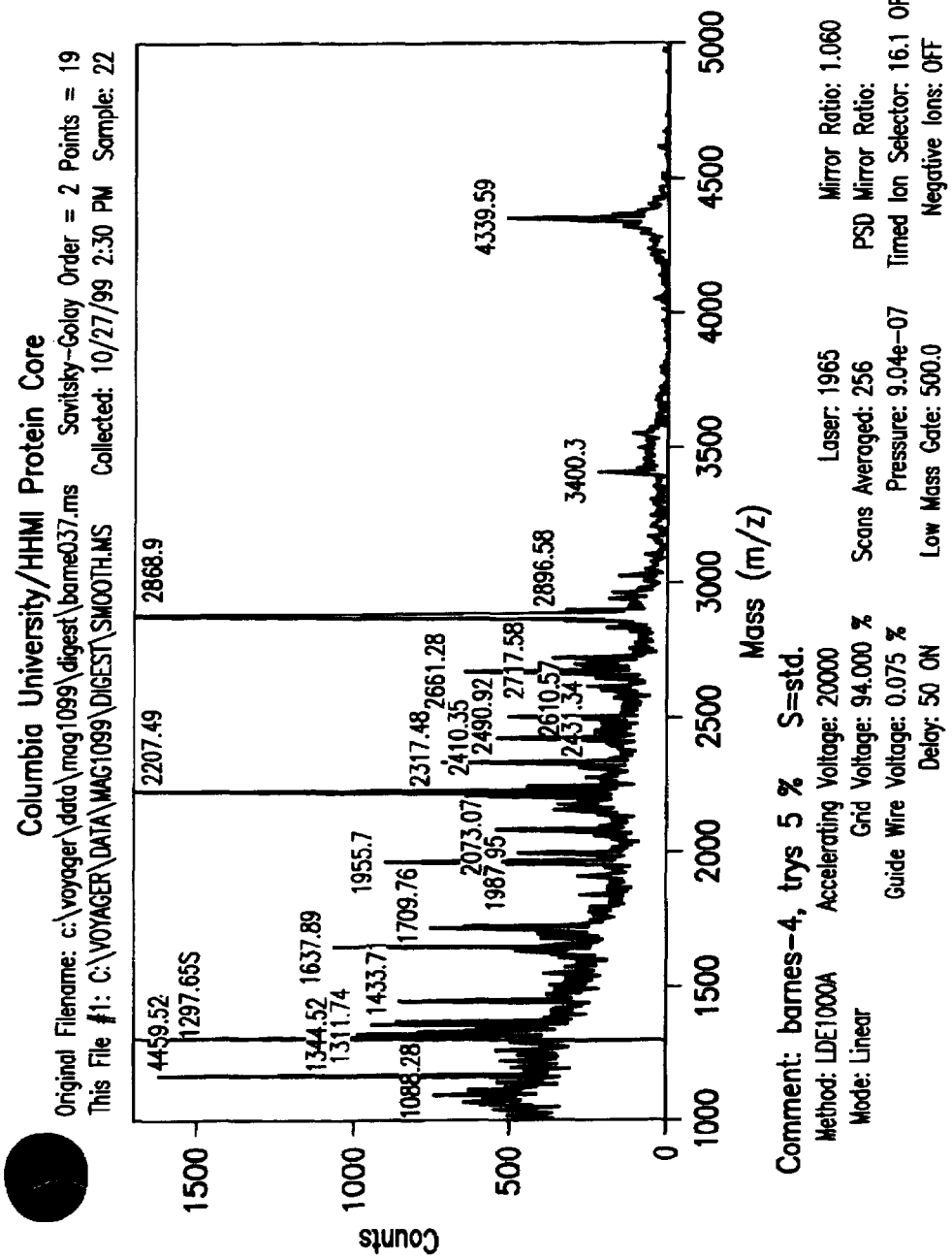
Figure 7E:
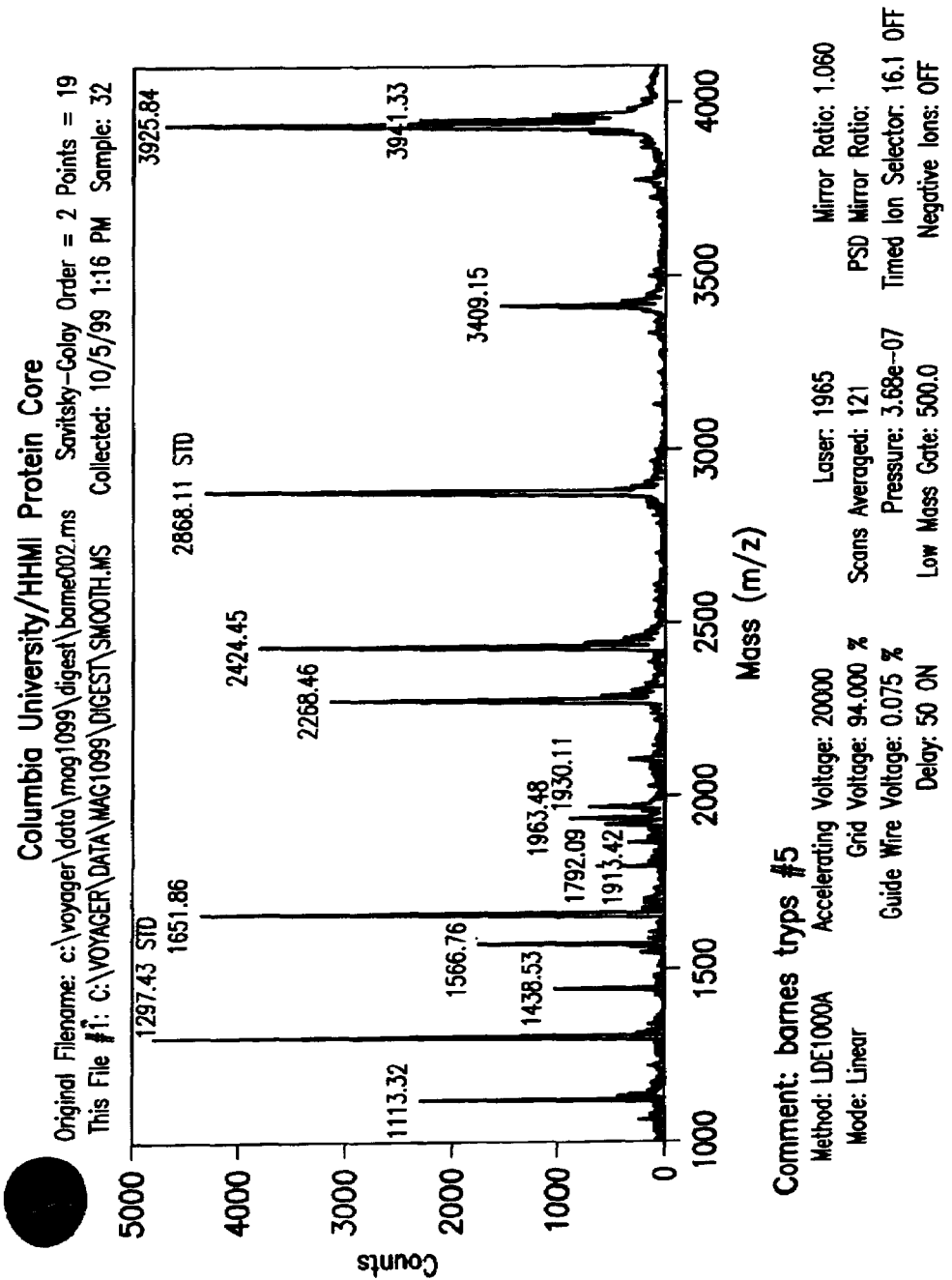
Figure 7F:
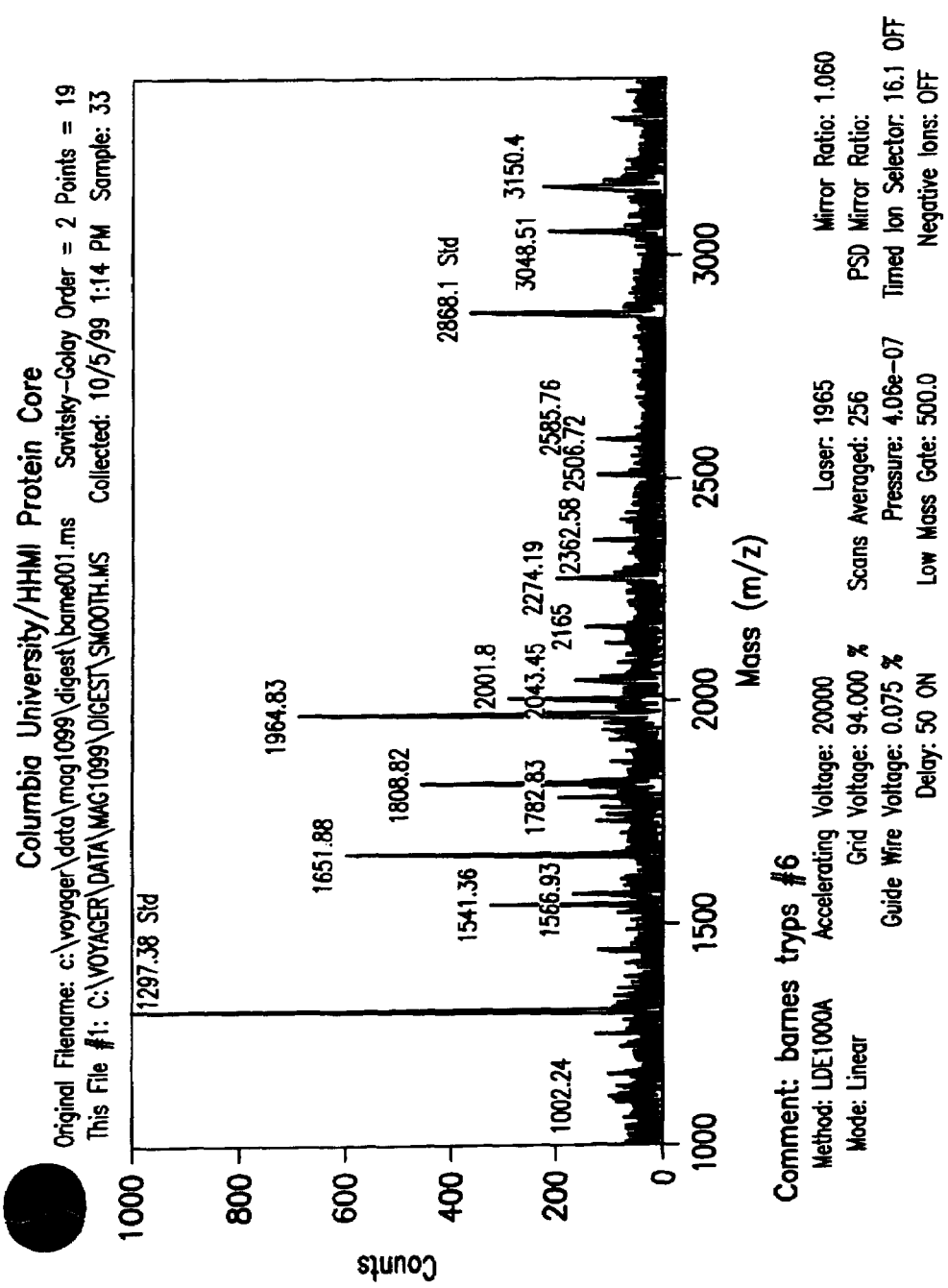
Figure 7G:
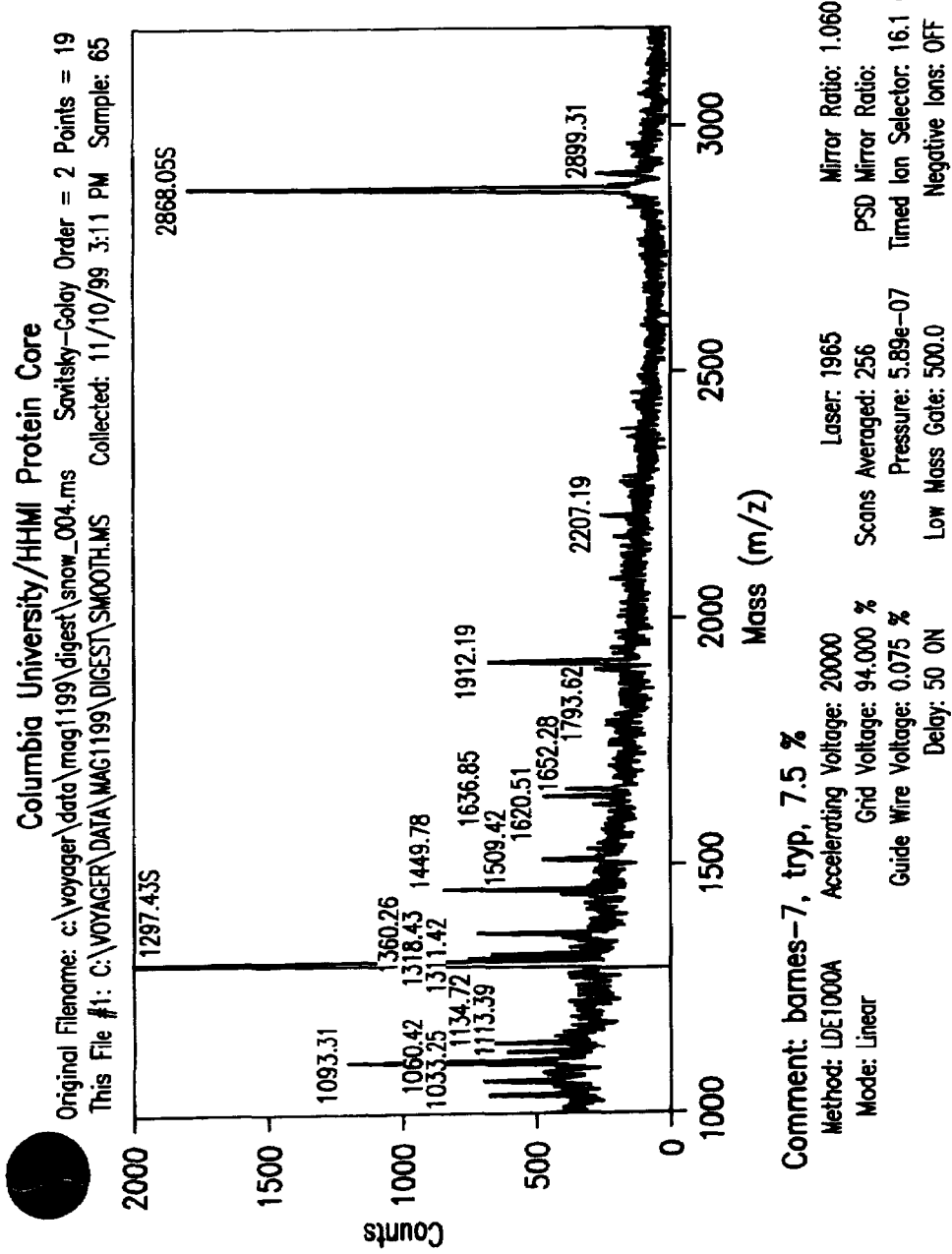
Figure 7H:
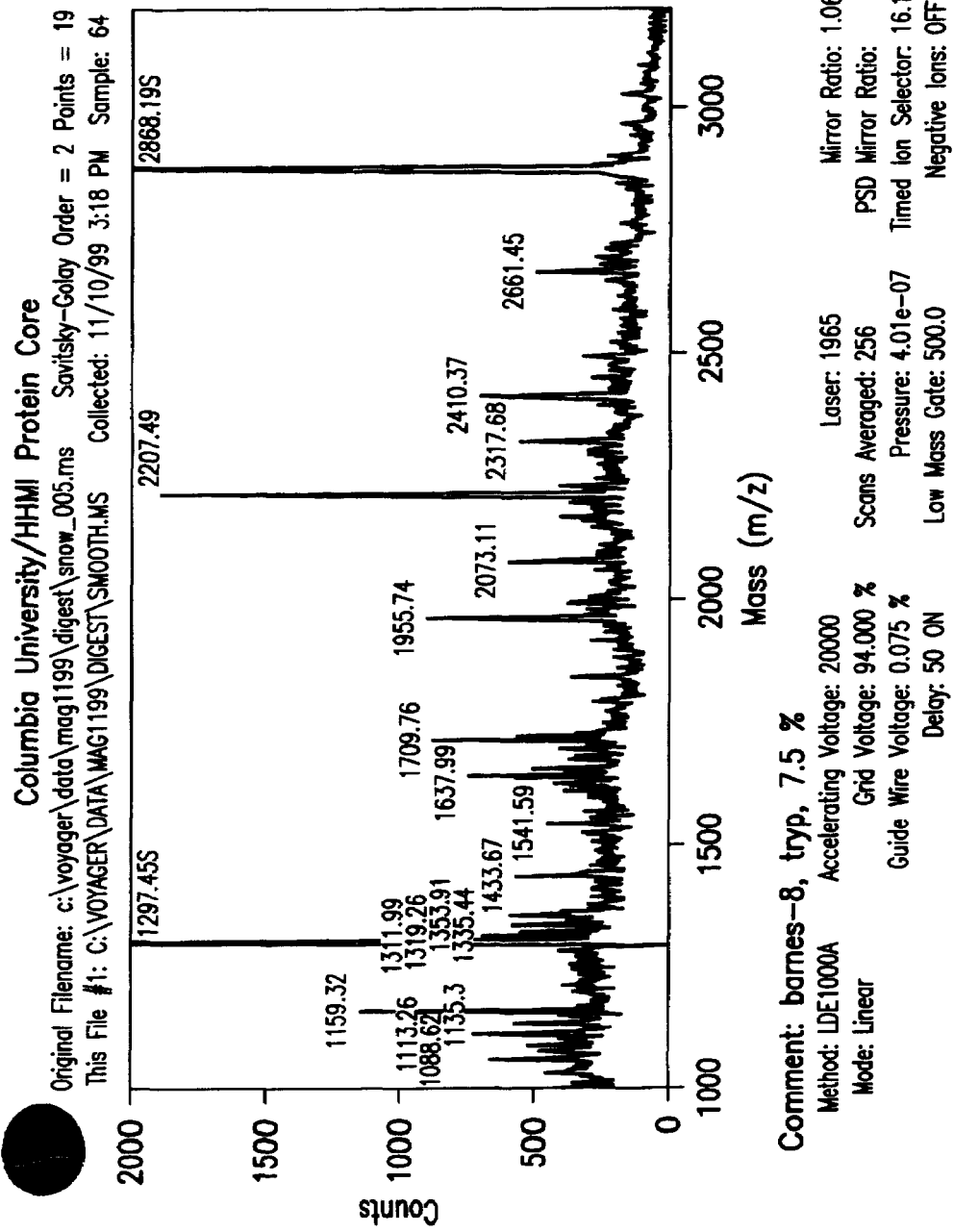
Figure 7I:
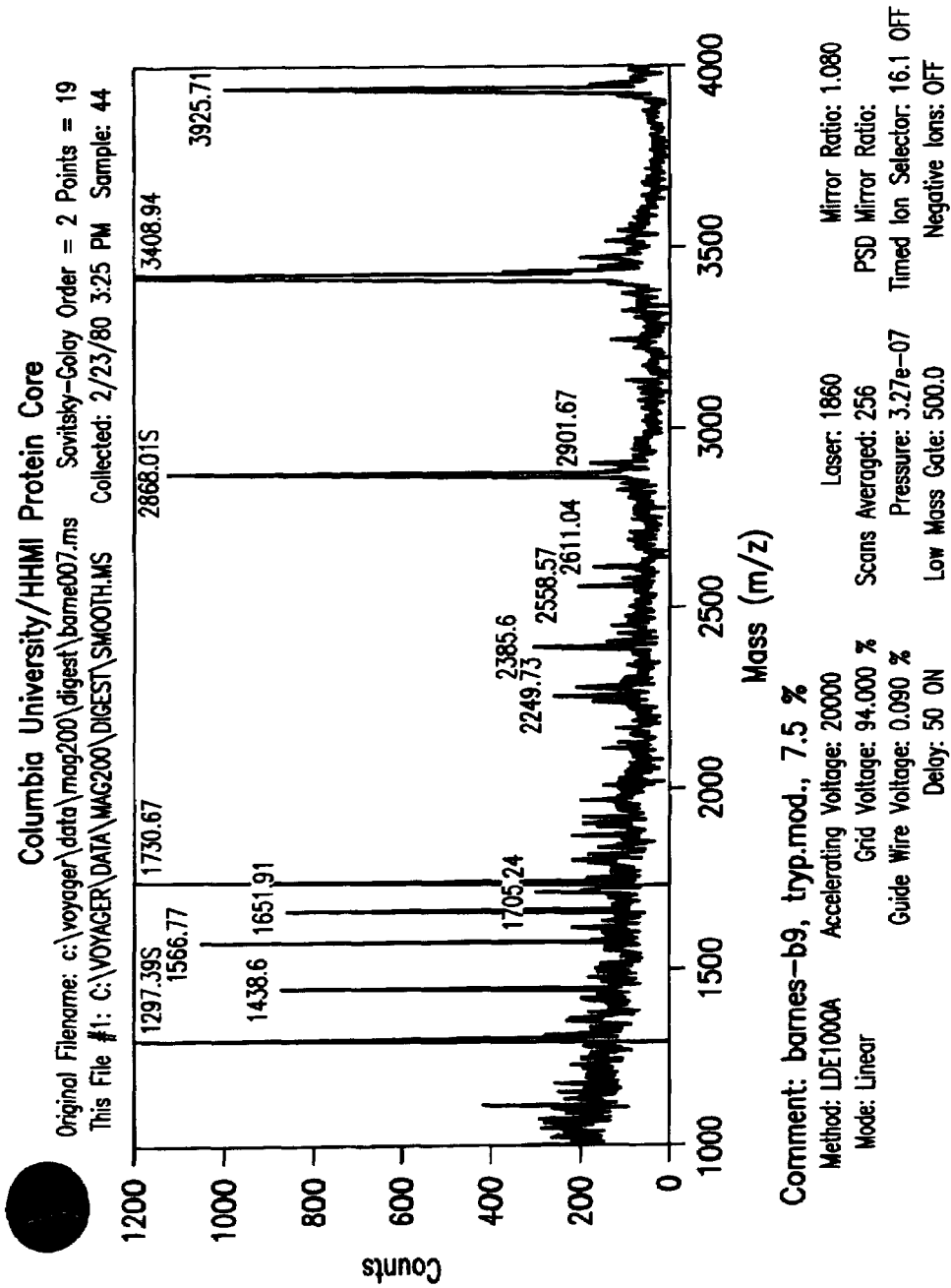
Figure 7J:
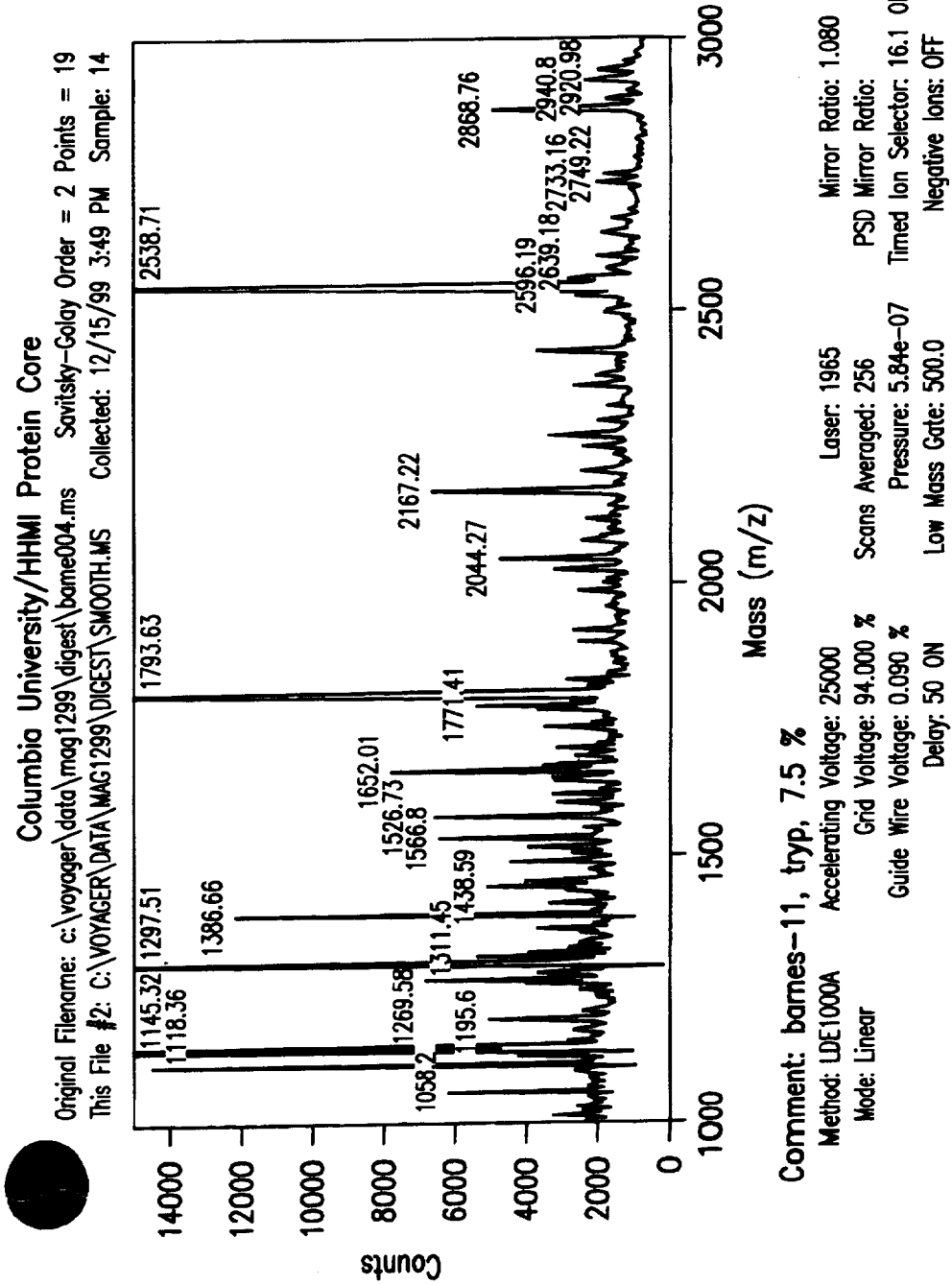
Figure 7K:
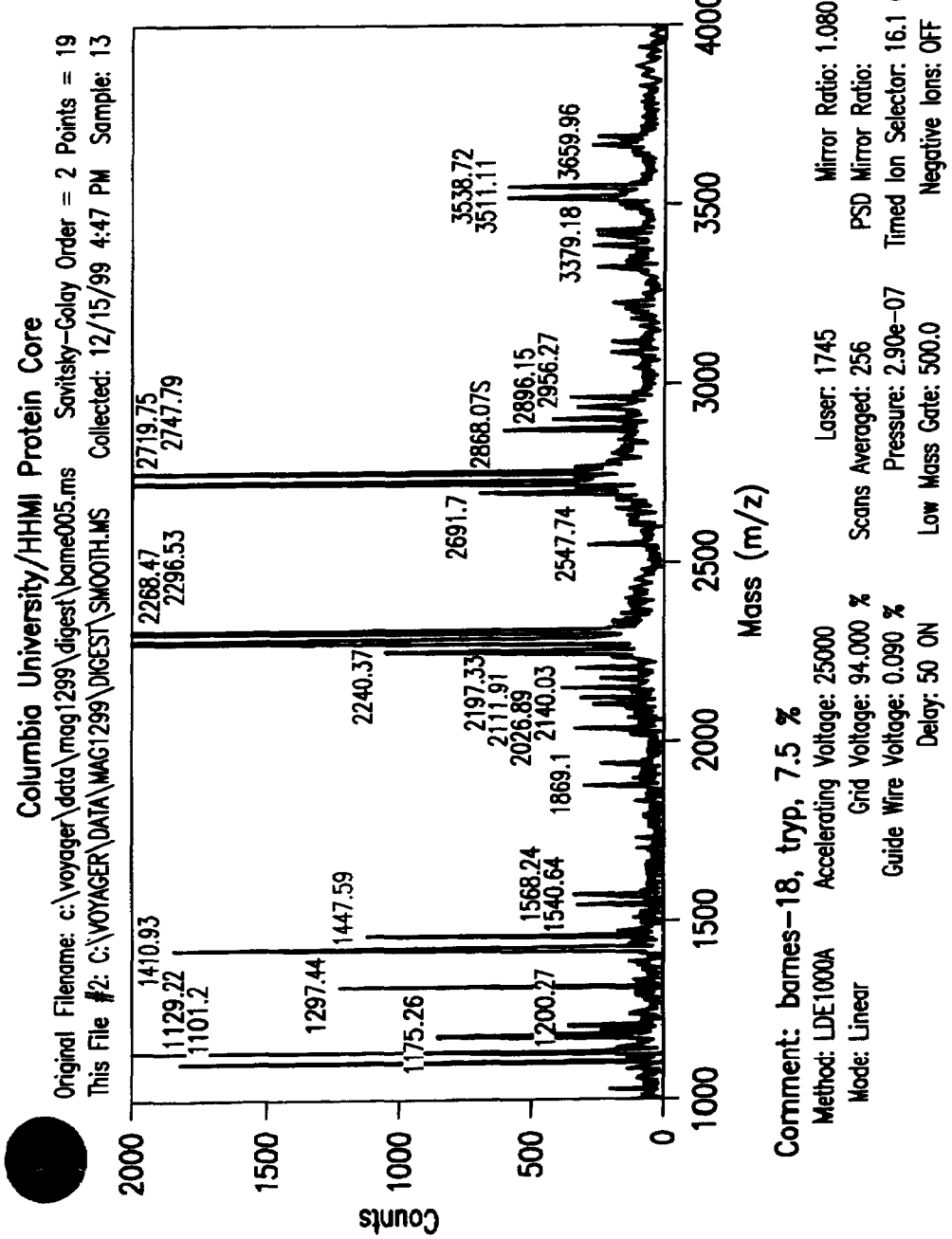
Figure 7L:
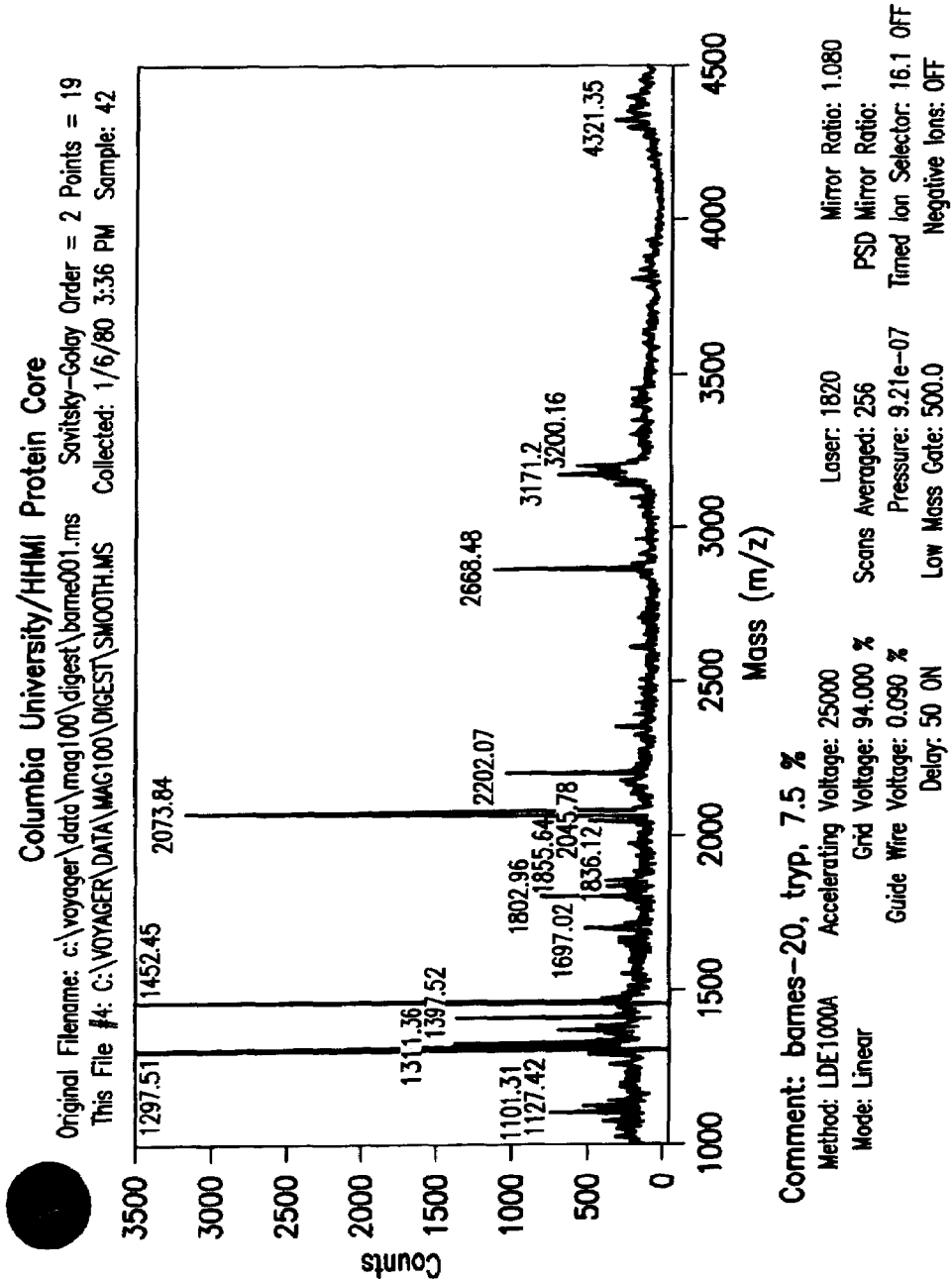
Figure 7M:
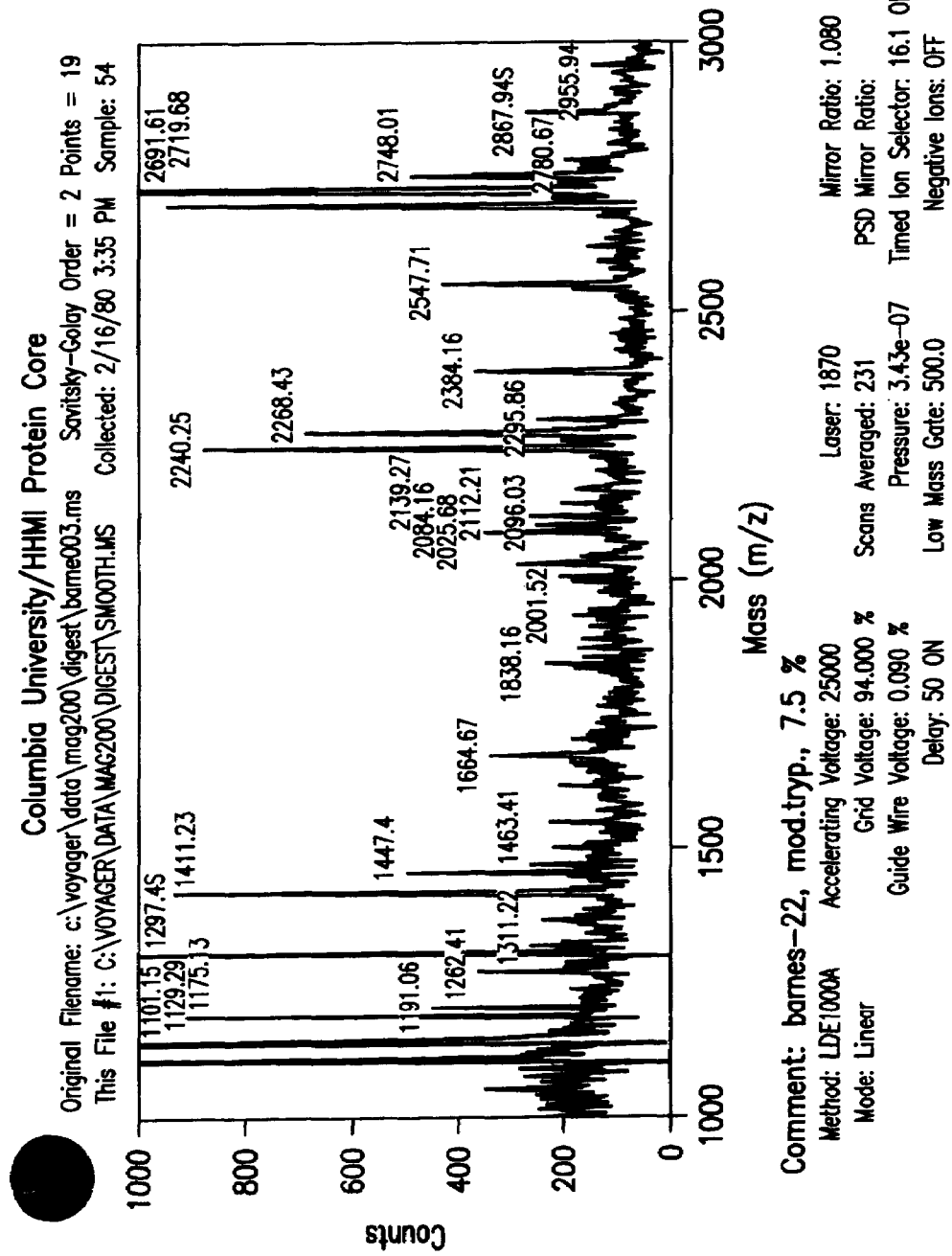
Figure 7N:
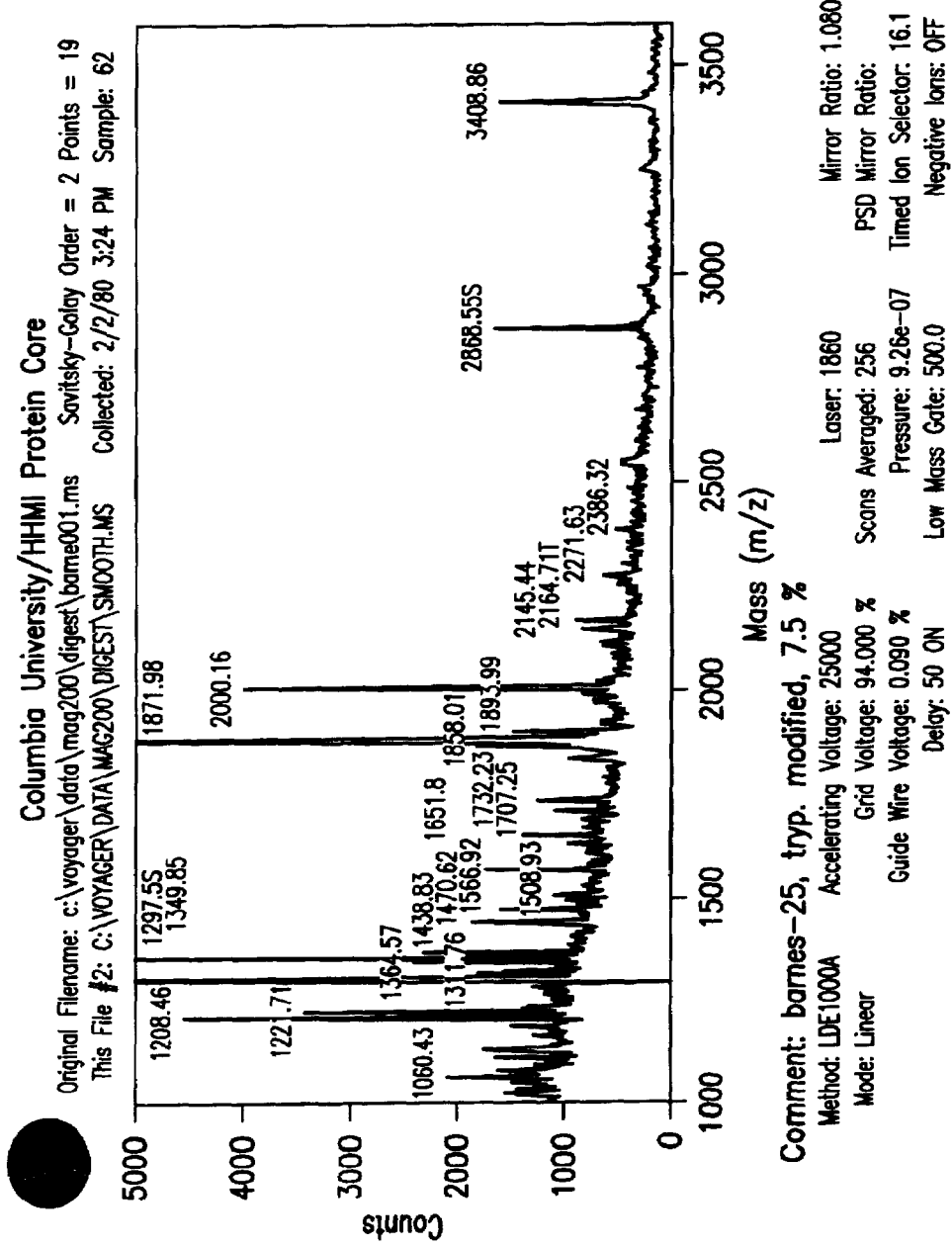
Figure 70:
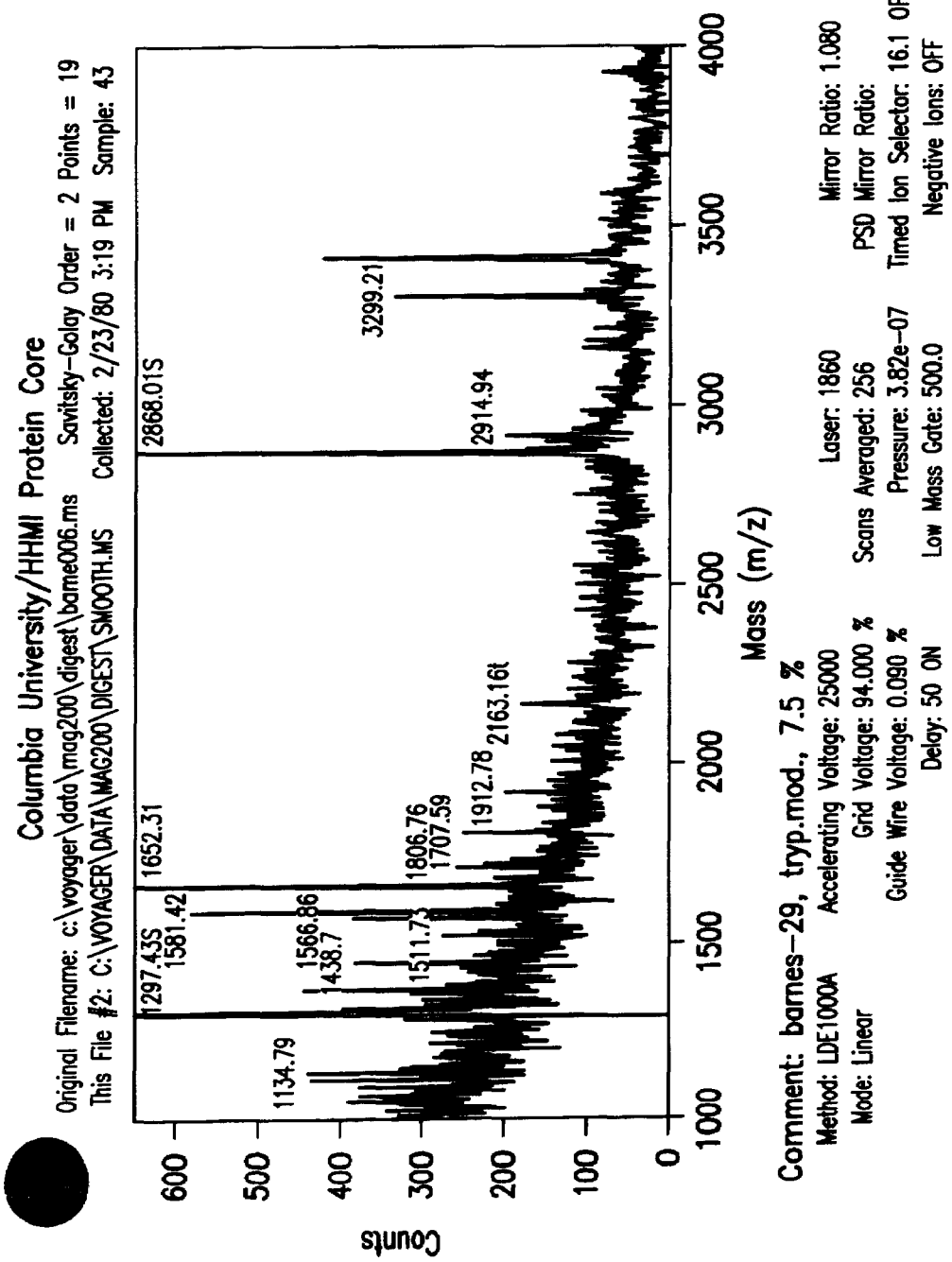

The same tryptic protein fragments were analyzed by mass spectrometry and the mass spectrograms are shown in FIGS. 7A–O. The tabulated results and homologies are shown in FIGS. 16A–F, which provide identification information for the bands identified in FIGS. 3–4. As above, assignment of spot identity may be tentative based on species differences and post translational modifications. A summary of all protein identifications for id gels is shown in FIG. 4.

Figure 17A:
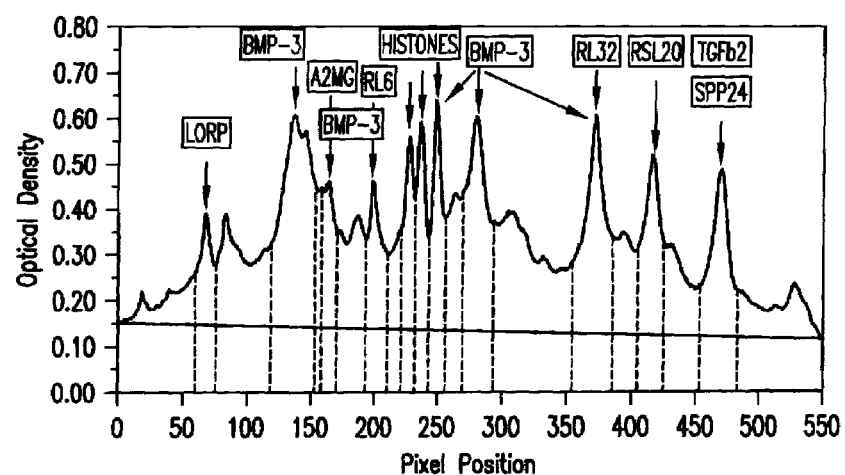
FIGS. 17A–B are an SDS-gel (FIG. 17B) and a scanning densitometer scan (FIG. 17A) of the same gel for a protein mixture according to an embodiment of the present invention.
Figure 17B:

The identified protein components of BP, as described in FIGS. 15A–B, 16A–F and 19A–C, were quantified as shown in FIGS. 17A and 17B. FIG. 17B is a stained SDS-PAGE gel of BP and FIG. 17A represents a scanning densitometer trace of the same gel. The identified proteins were labeled and quantified by measuring the area under the curve. These results are presented in FIG. 18 as a percentage of the total peak area.

Thus, there are 11 major bands in the BP SDS-PAGE gel, representing about 60% of the protein in BP. The identified proteins fall roughly into three categories: the ribosomal proteins, the histones, and growth factors, including bone morphogenic factors (BMPs). It is expected that he ribosomal proteins may be removed from the BP without loss of activity, since these proteins are known to have no growth factor activity. Upon this separation, the specific activity is expected to increase correspondingly.

It is expected that the histone and ribosomal proteins may be removed from the BP with no resulting loss, or even with an increase, in specific activity. It is expected that histones can removed from the BP cocktail by immunoaffinity chromatography, using either specific histone protein antibodies or a pan-histone antibody. The histone depleted BP (BP-H) produced in this manner may be suitable for wound healing. Similarly, the mixture produced when the known ribosomal proteins are stripped from the BP cocktail (BP-R) may be suitable for wound healing.

An SDS-PAGE gel of BP was also analyzed by Western immunoblot with a series of antibodies, as listed in FIG. 14. Visualization of antibody reactivity was by horseradish peroxidase conjugated to a second antibody and using a chemiluminescent substrate. Further, TGF-β1 was quantified using commercially pure TGF-β1 as a standard and was determined to represent less than 1% of the BP protein The antibody analysis indicated that each of the proteins listed in FIG. 14 is present in BP.

Figure 5:
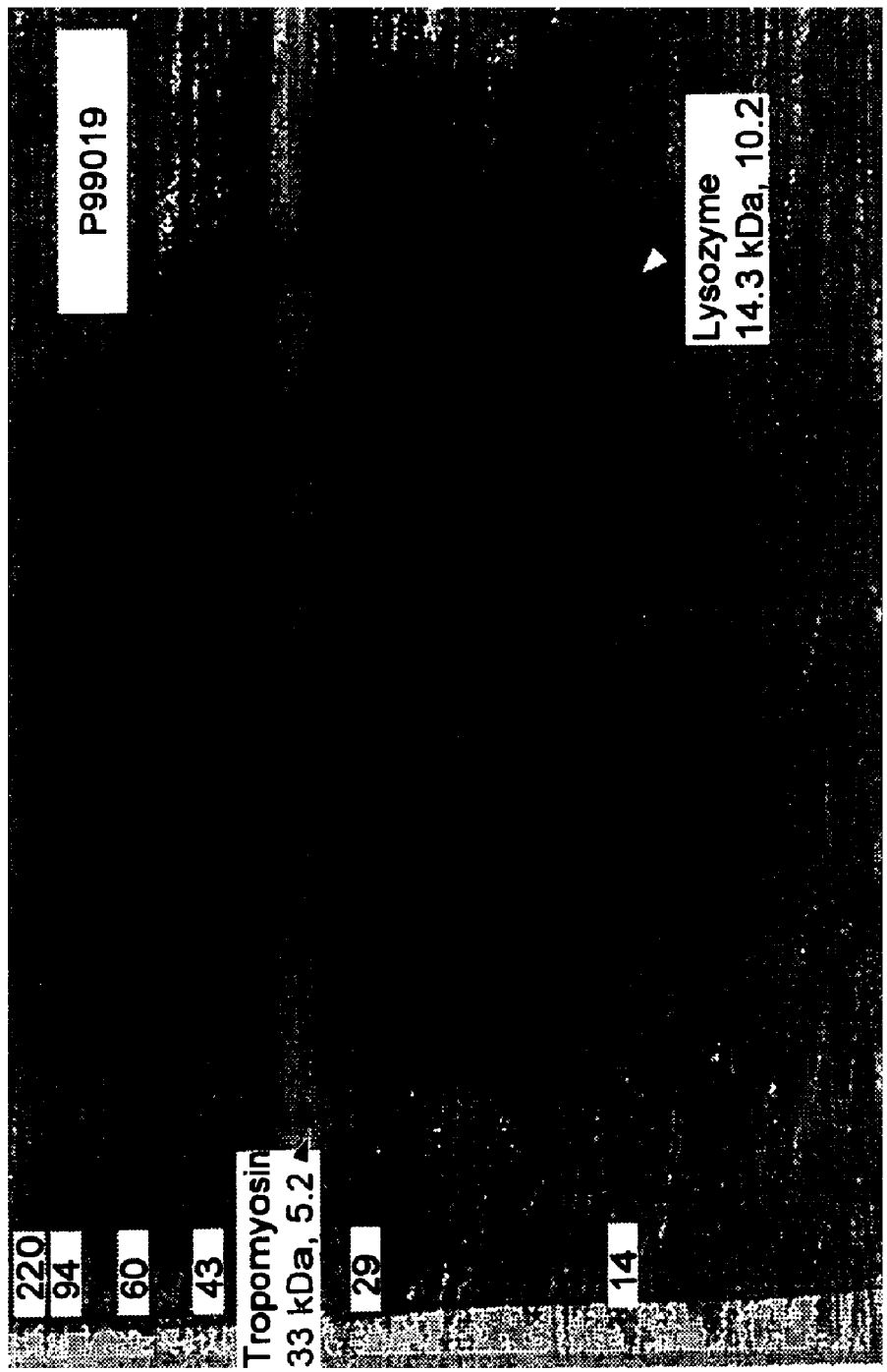
FIG. 5 is a two dimensional (2-D) SDS-PAGE gel of a protein mixture according to an embodiment of the present invention with internal standards indicated by arrows.
Figure 6:
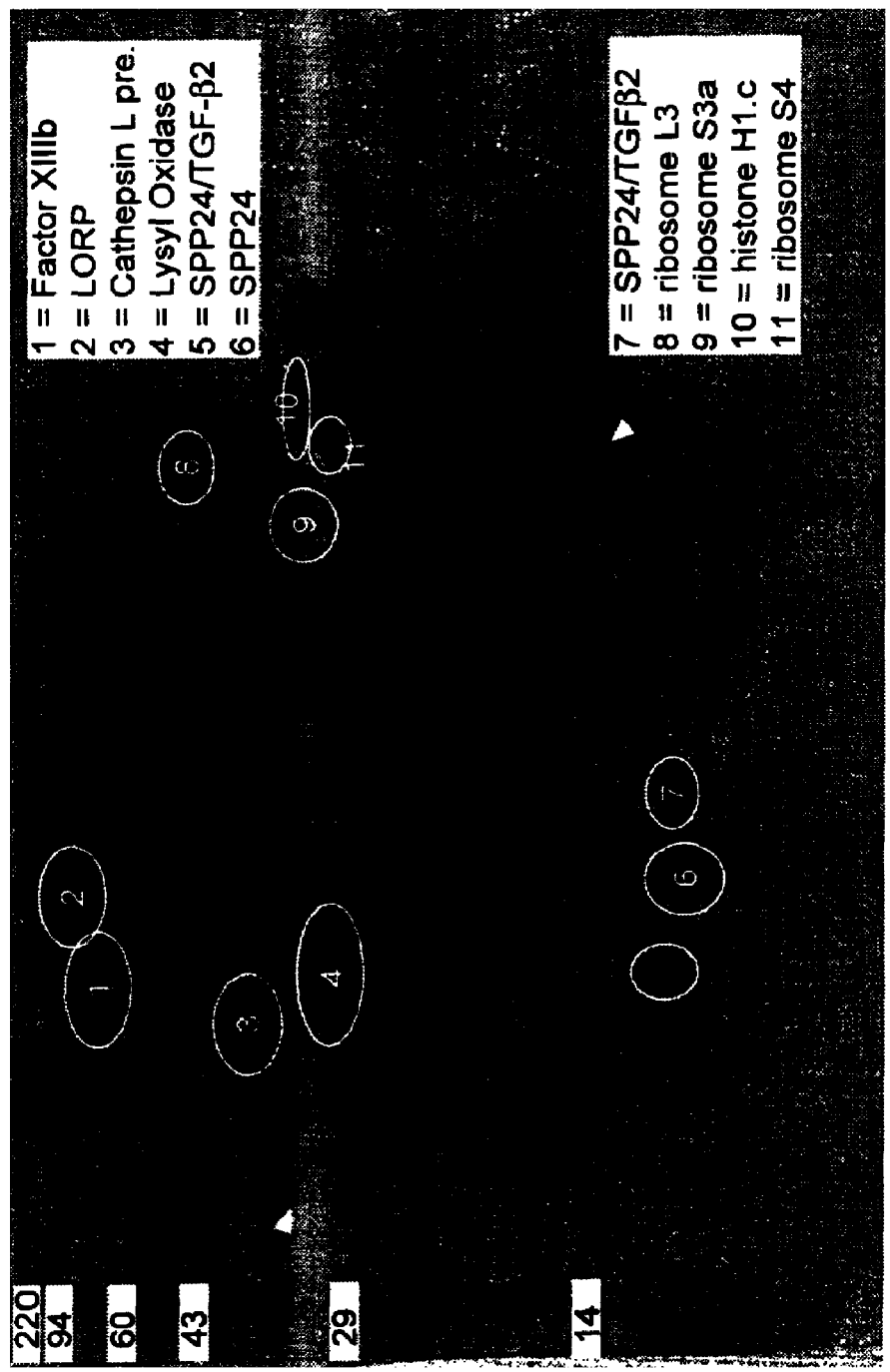
FIG. 6 is a 2-D SDS-PAGE gel of a protein mixture according to an embodiment of the present invention with circled proteins identified as in the legend.

The BP was further characterized by 2-D gel electrophoresis, as shown in FIGS. 5–6. The proteins are separated in horizontal direction according to charge (pI) and in the vertical direction by size as described in two-dimensional electrophoresis adapted for resolution of basic proteins was performed according to the method of O'Farrell et al. (O'Farrell, P. Z., Goodman, H. M. and O'Farrell, P. H., Cell, 12: 1133–1142, 1977) by the Kendrick Laboratory (Madison, Wis.). Two-dimensional gel electrophoresis techniques are known to those of skill in the art. Non-equilibrium pH gradient electrophoresis ("NEPHGE") using 1.5% pH 3.5–10, and 0.25% pH 9–11 ampholines (Amersham Pharmacia Biotech, Piscataway, N.J.) was carried out at 200 V for 12 hrs. Purified tropomyosin (lower spot, 33,000 KDa, pI 5.2), and purified lysozyme (14,000 KDa, pI 10.5–11) (Merck Index) were added to the samples as internal pI markers and are marked with arrows.

After equilibration for 10 min in buffer "0" (10% glycerol, 50 mM dithiothreitol, 2.3% SDS and 0.0625 M tris, pH 6.8) the tube gel was sealed to the top of a stacking gel which is on top of a 12.5% acrylamide slab gel (0.75 mm thick). SDS slab gel electrophoresis was carried out for about 4 hrs at 12.5 mA/gel.

After slab gel electrophoresis two of the gels were coomassie blue stained and the other two were transferred to transfer buffer (12.5 mM Tris, pH 8.8, 86 mM Glycine, 10% MeoH) transblotted onto PVDF paper overnight at 200 mA and approximately 100 volts/two gels. The following proteins (Sigma Chemical Co., St. Louis, Mo.) were added as molecular weight standards to the agarose which sealed the tube gel to the slab gel: myosin (220,000 KDa), phosphorylase A (94,000 KDa), catalase (60,000 KDa), actin (43,000 KDa), carbonic anhydrase (29,000 KDa) and lysozyme (14,000 KDa). FIG. 5 shows the stained 2-D gel with size standards indicated on the left. Tropomyosin (left arrow) and lysozyme (right arrow) are also indicated.

The same gel is shown in FIG. 6 with several identified proteins indicated by numbered circles. The proteins were identified by mass spectrometry and amino acid sequencing of tryptic peptides, as described above. The identity of each of the labeled circles is provided in the legend of FIG. 6 and the data identifying the various protein spots is presented in FIGS. 19A–C.

Figure 8:
FIG. 8 is a 2-D gel Western blot of a protein mixture according to an embodiment of the present invention labeled with anti-phosphotyrosine antibody.

Because several of the proteins migrated at more than one size (e.g., BMP-3 migrating as 6 bands) investigations were undertaken to investigate the extent of post-translation modification of the BP components. Phosphorylation was measured by anti-phosphotyrosine immunoblot and by phosphatase studies. FIG. 8 shows a 2-D gel, electroblotted onto filter paper and probed with a phosphotyrosine mouse monoclonal antibody by SIGMA (# A-5964). Several proteins were thus shown to be phosphorylated at one or more tyrosine residues.

Figure 9A:
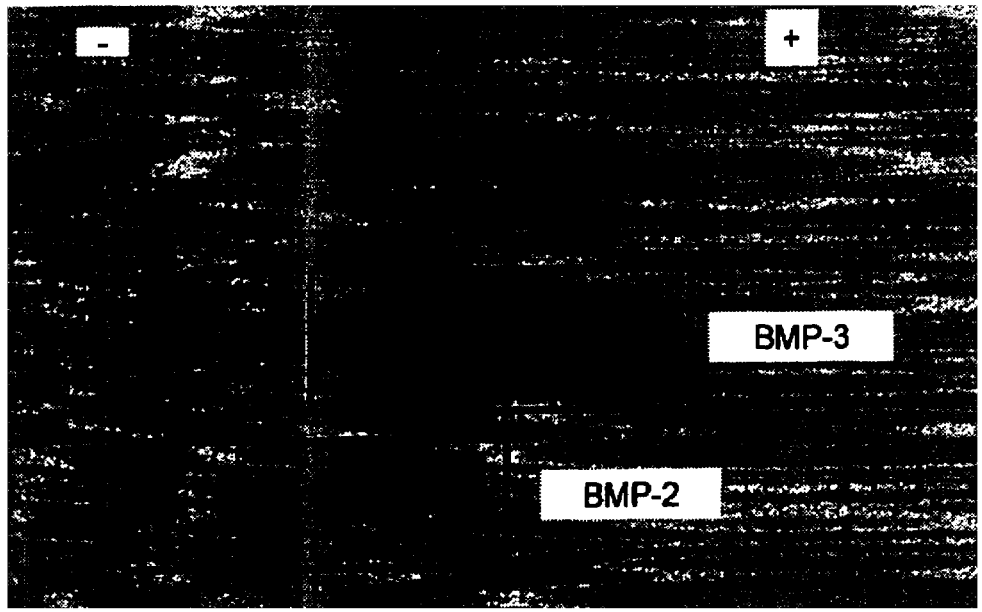
FIGS. 9A–D are 2-D gel Western blots of a protein mixture according to an embodiment of the present invention, labeled with indicated antibodies.
Figure 9B:
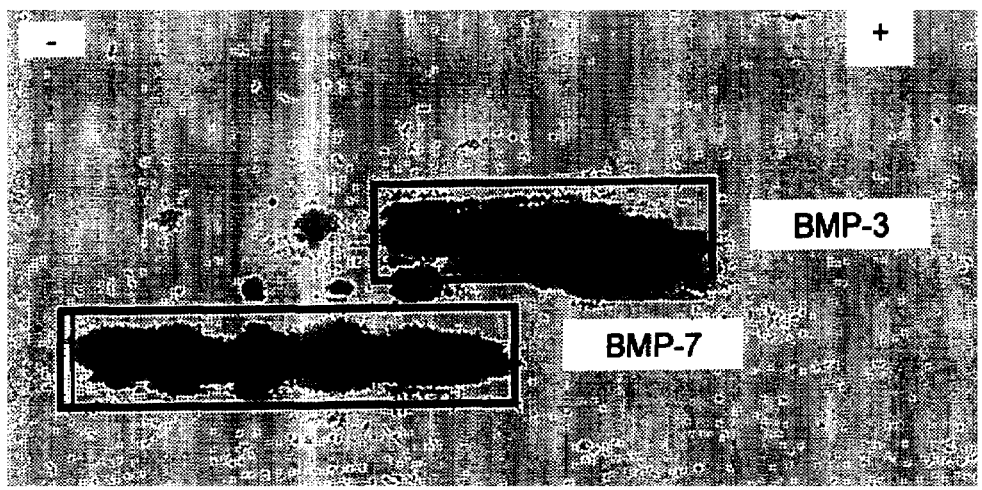
Figure 9C:
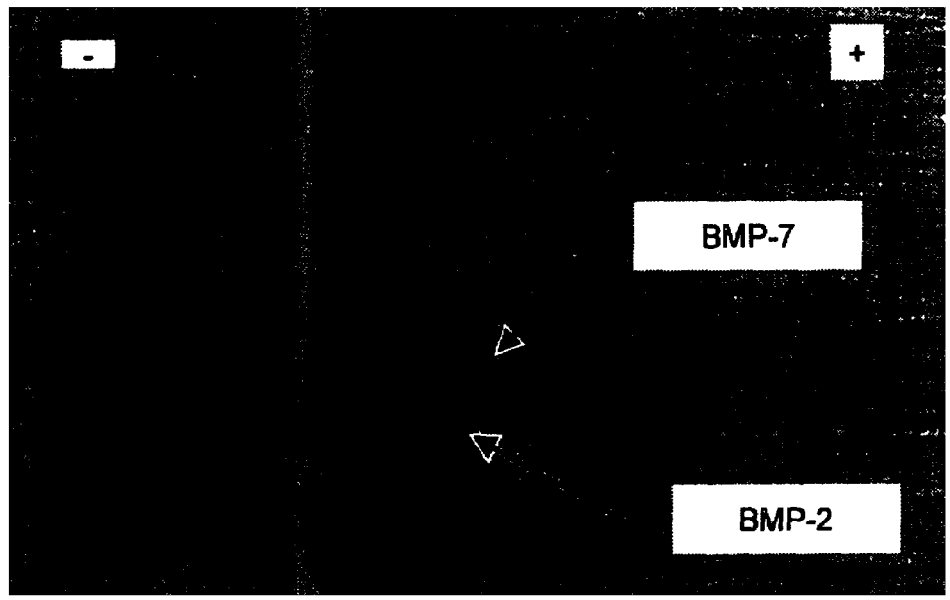
Figure 9D:
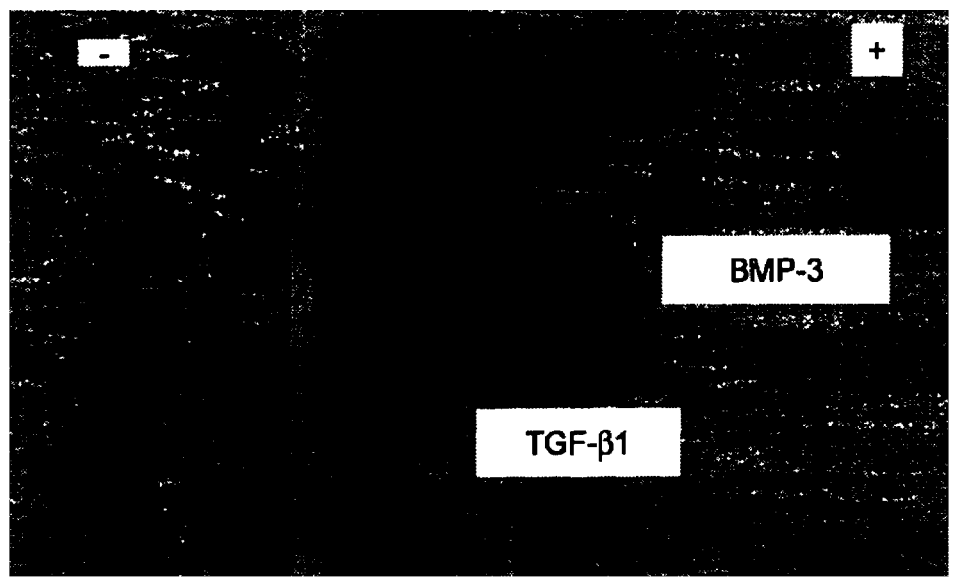

Similar 2-D electroblots were probed with BP component specific antibodies, as shown in FIGS. 9A–D. The filters were probed with BMP-2, BMP-3 (FIG. 9A), BMP-3, BMP-7 (FIG. 9B), BMP-7, BMP-2 (FIG. 9C), and BMP-3 and TGF-β1 (FIG. 9D). Each shows the characteristic, single-size band migrating at varying pI, as is typical of a protein existing in various phosphorylation states.

For the phosphatase studies, BP in 10 mM HCl was incubated overnight at 37° C. with 0.4 units of acid phosphatase (AcP). Treated and untreated samples were added to lyophilized discs of type I collagen and evaluated side by side in the subcutaneous implant rat bioassay, as previously described in U.S. Pat. Nos. 5,290,763, 5,563,124 and 5,371,191. Briefly, 10 (g of BP in solution was added to lyophilized collagen discs and the discs implanted subcutaneously in the chest of a rat. The discs were then recovered from the rat at 2 weeks for the alkaline phosphotase ("ALP" —a marker for bone and cartilage producing cells) assay or at 3 weeks for histological analysis. For ALP analysis of the samples, the explants were homogenized and levels of ALP activity measured using a commercial kit. For histology, thin sections of the explant were cut with a microtome, and the sections stained and analyzed for bone and cartilage formation.

Both native- and phosphatase-treated BP samples were assayed for morphogenic activity by mass of the subcutaneous implant (explant mass) and ALP score. The results showed that AcP treatment reduced the explant mass and ALP score from 100% to about 60%. Thus, phosphorylation is important for BP activity.

Figure 10:
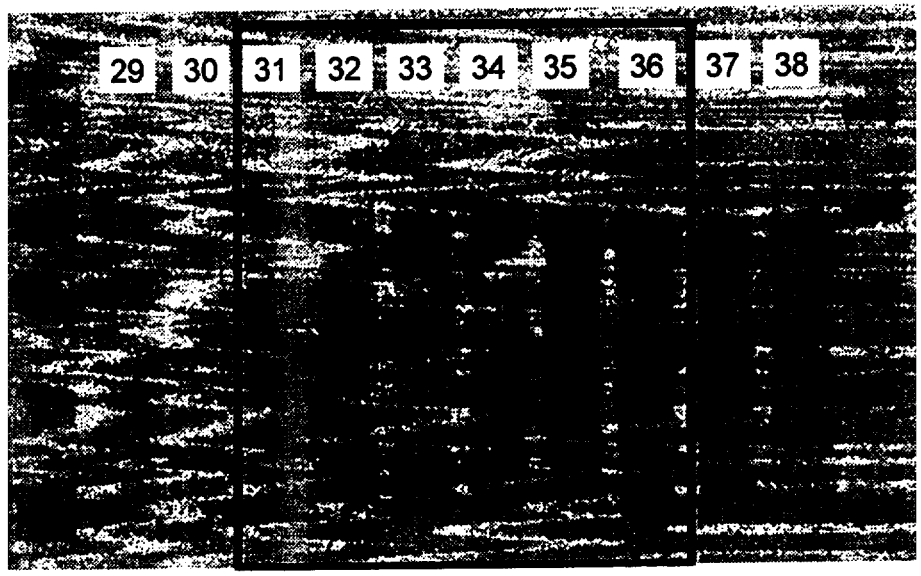
FIG. 10 is a PAS (periodic acid schiff) stained SDS-PAGE gel of HPLC fractions of a protein mixture according to an embodiment of the present invention.
Figure 11:
FIG. 11 is an anti-BMP-7 stained SDS-PAGE gel of a PNGase F treated protein mixture according to an embodiment of the present invention.
Figure 12:
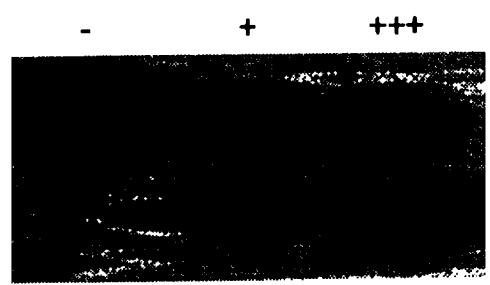
FIG. 12 is an anti-BMP-2 stained SDS-PAGE gel of a PNGase F treated protein mixture according to an embodiment of the present invention.
Figure 13A:
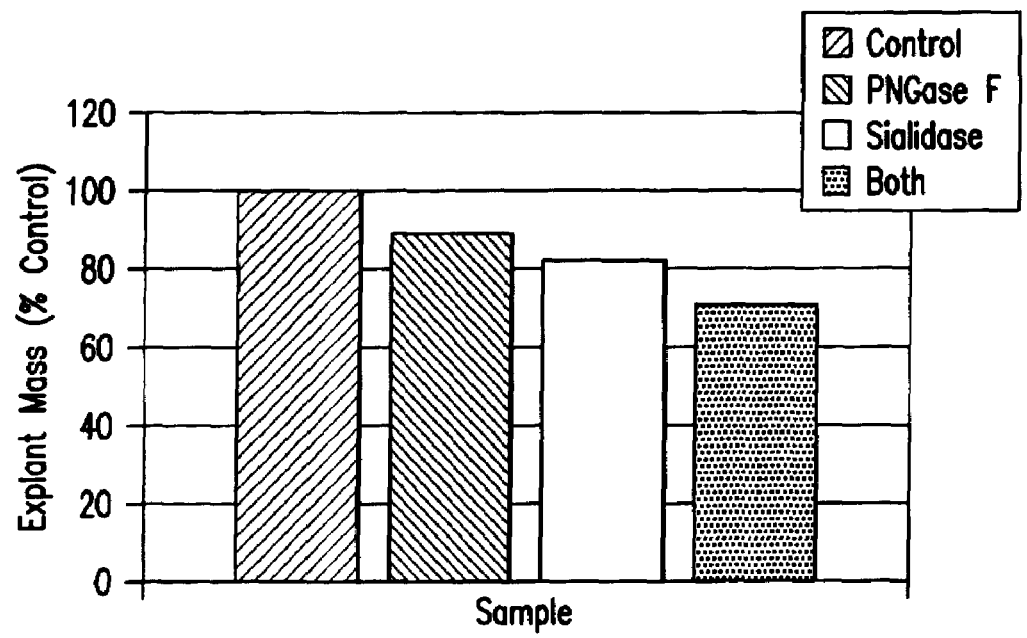
FIGS. 13A–B are bar charts showing explant mass of glycosylated components in a protein mixture according to an embodiment of the present invention (FIG. 13A) and ALP score (FIG. 13B) of the same components.
Figure 13B:
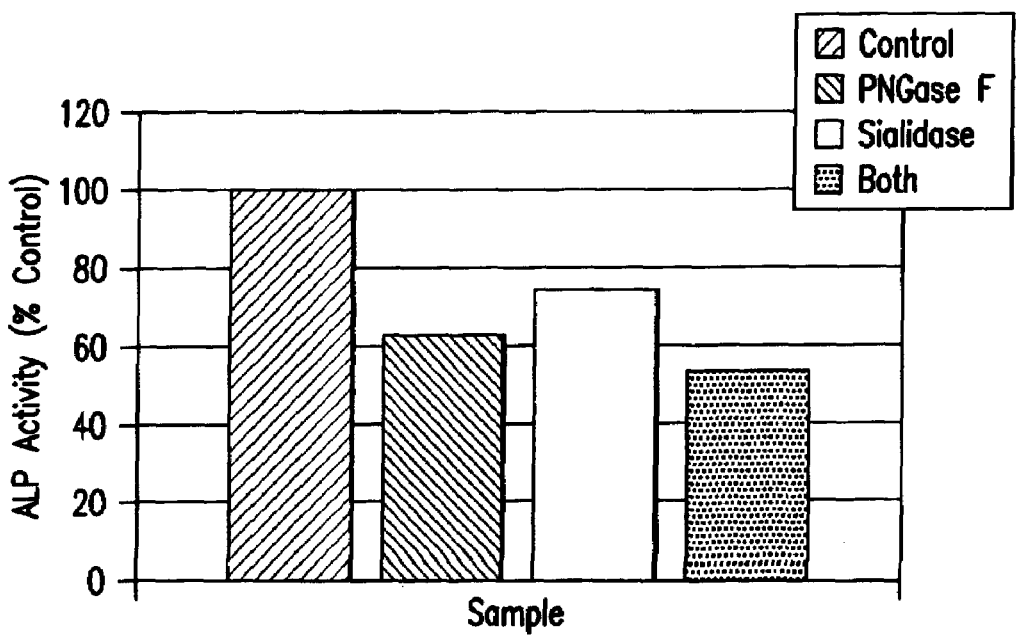

The BP was also analyzed for glycosylation. FIG. 10 shows an SDS-PAGE gel stained with periodic acid schiff (PAS)—a non-specific carbohydrate stain, indicating that several of the BP components are glycosylated (starred protein identified as BMP-3). FIGS. 11–12 show immunodetection of two specific proteins (BMP-7, FIG. 14 and BMP-2, FIG. 15) treated with increasing levels of PNGase F (Peptide-N-Glycosidase F). Both BMP-2 and BMP-7 show some degree of glycoslyation in BP, but appear to have some level of protein resistant to PNGase F as well (plus signs indicate increasing levels of enzyme). Functional activity of PNGase F and sialadase treated samples were assayed by explant mass and by ALP score, as shown in FIGS. 13A and 13B, which shows that glycosylation is required for full activity.

In summary, BMPs 2, 3 and 7 are modified by phosphorylation and glycosylation. These post-translation modifications affect protein morphogenic activity, 33% and 50% respectively, and care must be taken in preparing BP not to degrade these functional derivatives.

The methods disclosed and claimed herein can be made and executed without undue experimentation in light of the present disclosure. While the compositions and methods of this invention have been described in terms of preferred embodiments, it will be apparent to those of skill in the art that variations may be applied to the method and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The following examples are intended to be merely illustrative, and do not limit the scope of the claimed invention.

EXAMPLE 1

Figure 20A:
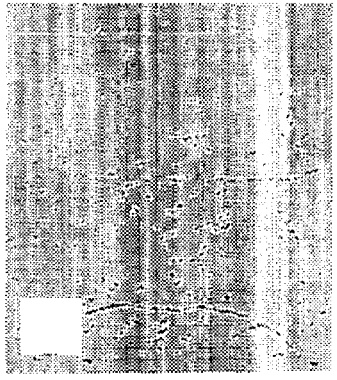
FIGS. 20A–C show the results of a quail chorioallantoid membrane (CAM) angiogenesis assay of a protein mix according to the present invention.
Figure 20B:
Figure 20C:

Quail chorioallantoic membrane (CAM) was in the manner described in "A Novel Assay of Angiogenesis in the Quail Chorioallantoic Membrane: Stimulation by bFGF and Inhibition by Angiostatin According to Fractal Dimension and Grid Intersection," Parsons-Wingerter P., Dwai B., Yang M C., Elliot K E., Milaninia A., Redlitz A., Clark J. and Sage E. H. Fertilized Japanese quail eggs (*Coturnix coturnix japonica*) were opened onto Petri dishes on day 3 postincubation (FIG. 20A). After 4 days of culture, a BDAP mixture, diluted in PBS/ovalubumin prewarmed to 37° C., was distributed evenly onto the surface of the CAM. After 24 hours of incubation, the CAM's were fixed, dissected and photographed (FIG. 20B) at 10× magnification to visualize the arterial vascular tree, including endstage vessels. Digital images of triplicate CAM specimens were acquired at 10× magnification in grayscale, binarized to black-and-white, and skeletonized (FIG. 20C). The vessel branching pattern was analyzed and quantified by the fractal dimension.

Figure 21:
FIG. 21 shows the vascular growth in the CAM of FIGS. 20A–C.

The photographs in FIG. 21 are representative digital binarized images of CAMs exposed to 10 μg/ml dose of growth factor for 24 hours. Quantitative data corresponding to these images were acquired by analyzing the skeletonized images and determining the fractal dimension of the branched vascular pattern. Data were pooled from two separate experiments consisting of three CAMs per experiment. Exposure to BDAP resulted in 124% greater mean angiogenic stimulation over the basal rate (defined as the change in fractal dimension in untreated controls) versus a 43% increase over basal rate for bFGF-treated CAMs. ($p<0.006$).

It is hypothesized that this combination of factors acts synergistically to facilitate the proliferation, migration and differentiation processes essential to angiogenesis more effectively than a single factor.

Preliminary data suggest that other fractions of proteins eluted from bone are also angiogenic. An assay of a second protein mixture, BDAP-2, defined as the fraction eluting at an acetonitrile concentration of from about 37 to about 39.5 percent, membrane was performed on quail chorioallantoic membrane (CAM) using the same protocol as that described above with respect to the BDAP assay. The angiogenic response in the quail CAM assay was 86 percent greater than the basal angiogenic rate after treatment with this alternative protein mix.

EXAMPLE 2

Canine Myocardial Angiogenesis Pilot Study

Four adult mongrel dogs of either sex, weighing 21–26 kg, were anesthetized and a left thoracotomy performed through the fifth intercostal space. All visible epicardial collaterals connecting LAD diagonals to circumflex or right coronary arteries were ligated to minimize collateral flow to the LAD territory and an ameroid constrictor was placed on the proximal to the first diagonal branch. After completing the procedure, 0, 10 or 100 µg BDAP was injected in a 0.1 cc volume of povidone (polyvinylpyrrolidone), as polymer microspheres suspended in povidone, or in collagen gel for a total of nine injections. Each series of injections was administered in the ischemic LAD region of the left ventricle, as well as in a non-ischemic LCX region. The chest was closed and the animal was allowed to recover.

In order to provide an index of cellular proliferation at multiple time points after the initial surgery, bromodeoxyuridine (BrdU, 25 mg/kg, Sigma, St. Louis, Mo.) was administered subcutaneously on post-operative days 2, 4, 6, 8, 10, 12, 14 and 21. After two or six weeks, the dogs were euthanized and the hearts explanted and cut into samples. Samples were fixed and serial sections, 4–5 microns thick, were cut and stained with Masson's trichrome stain to evaluate the general morphology of the myocardium. Sister sections were stained using standard immunohistochemical techniques with antibodies against bromodeoxyuridine (BrdU), PC10 proliferating cell nuclear antigen (PCNA), alpha smooth muscle actin (SMA) and Factor VIII using standard techniques.

Figure 22:
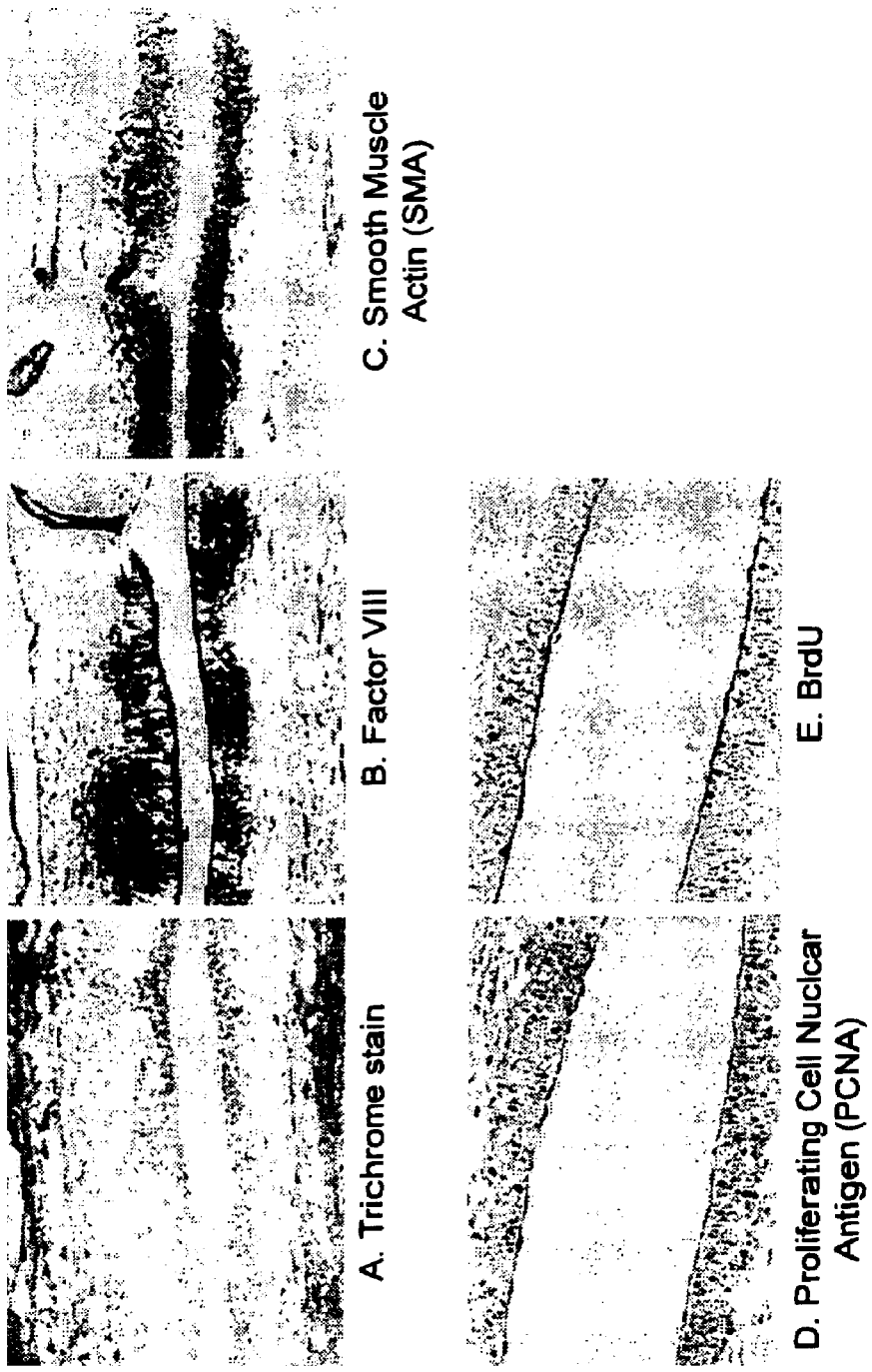
FIGS. 22A–E are histological sections of blood vessels formed in the canine myocardium following treatment with a protein mix in accordance with the present invention.

Initial histological data (FIGS. 22A–E) indicate that 10 or 100 micrograms of BDAP suspended in 0.1 cc povidone stimulated blood vessel formation within two weeks post injection. Whereas control sections showed no significant vessel formation and the needle tract was visible, BDAP-treated sections had several newly formed blood vessels, as evidenced by Masson's trichrome staining (FIG. 22A). Immunohistochemical staining demonstrated that these vessels are lined with endothelial cells (dark stain FIG. 22B) and surrounded by a layer of smooth muscle cells (brown stain FIG. 22C). PCNA- and BrdU-stained sections (FIGS. 22D–E) indicated that these vascular endothelial and smooth muscle cells are actively proliferating. Thus, based on the qualitative results of the canine study, it was concluded that BDAP stimulates formation of new differentiated blood vessels approximately 50–100 µm in diameter in canine myocardium. (Note, in FIG. 22A–C, 1 cm≈200 µm; in FIG. 22D–E, 1 cm≈40 µm).

EXAMPLE 3

Large Scale Canine Myocardial Ischemia Study

The purpose of this study was to determine the effects of intramyocardial injections of Sulzer's Growth Factor mixture (GFm, also called ProVascTM) in a canine model of chronic myocardial ischemia. 38 dogs underwent ameroid constrictor placement on the proximal LAD and ligation of visible epicardial vessels collateralizing the LAD territory. Three weeks later, during a second surgery, animals had intramyocardial injections of either placebo, GFm at a concentration of 1 mg/ml or GFm at a concentration of 10 mg/ml. Each injection consisted of 0.15 ml, injections were at a spatial density of~1/cm2 over the LAD region. Group assignments were random and investigators were blinded to group assignment until after the analysis of all test results. Animal survived for an additional 6 weeks. Assessments of regional blood flow (by color microspheres), angiography and echocardiography (rest and stress) were performed prior to and after treatment. Histology and necropsy were performed after sacrifice. Results of this prospective, blinded, multifaceted assessment of the effects of GFm showed that the agent has a significant effect on vascular growth assessed histologically and by angiographic criteria. There was no significant effect on blood flow during maximal vasodilatory stress, though technical limitations resulted in inclusion of only a small number of studies for the analysis of maximal blood flow. There was a slight reduction in regional wall motion score during maximum dobutamine stress in the high concentration group, though global resting function was not influenced by treatment.

Colored Microsphere Study

Dye-Trak® Colored Microspheres (15±0.1 µm diameter, suspension in saline solution, 0.5% Tween 80 and 0.1% Thimerosal as a bacteriostat; Triton Technology Inc., San Diego, Calif.) provide a non-radioactive method of measuring regional blood flow. These precision, highly uniform spheres are quantified by spectrophotometry and were used to determine coronary blood flow at rest and during maximum adenosine stress. After randomization of colors, resting blood flow was assessed using rapid infusion of a set of microspheres (COLOR 1, 2 ml, 6×10$^6$ spheres) through the previously placed left atrial line. Just prior to the infusion, withdrawal of arterial blood from the descending aortic line was instituted at a rate of 7 ml/min using a constant flow pump (infusion and withdraw pump, Harvard Apparatus Inc., Millis, Mass. that was calibrated prior to this set of studies); this withdrawal was continued for a total of 2 minutes (14 ml). To induce vasodilatory stress, adenosine (A-9251, Sigma Chemical Co., St. Louis, Mo.) was infused at a concentration and rate titrated to cause an approximately 20% decrease in mean arterial pressure. After achieving this blood pressure reduction, blood flow was assessed through infusion of a second color microsphere (COLOR 2).

Dobutamine Stress Echocardiography:

Within the same 20–22 day window, if possible on a different day, resting and stress echocardiography were performed in the conscious state. These were done using protocols to standardize echocardiographic windows and views. Animals were lying in a left lateral position and a peripheral venous line with stop cock and extension line was placed. A constant flow pump (Harvard Apparatus Inc., model 22, South Natick, Mass.) was loaded with a 60 ml syringe containing dobutamine in normal saline. The dobutamine infusion solution was prepared immediately prior to the experiment. The body weight multiplied by 0.048 provided the number of milliliters of a 250 mg/ml stock solution that was diluted with normal saline to a total volume of 60 ml. The syringe was connected to the infusion line. Each echocardiogram was performed by one of 3 experienced echocardiographers completely blinded to group assignment. Animal names, ID numbers, time and dobutamine infusion rates were annotated on the video recording of each study. Baseline recordings under resting conditions at 4 different levels (basal, mid-papillary, low-papillary and apical; see FIG. 7) at each dobutamine infusion rate were acquired (HP Sonos 5500®, S4 transducer 2–2.5 MHz, Hewlett Packard, Andover, Mass.) from a parasternal short axis window.

During dobutamine infusion, images of all four levels were recorded on standard VHS tape for off-line analysis. The experiment was terminated one dosing level after reaching a target heart rate greater than 200/min, or when new onset of wall motion abnormality was noted and persisted for longer than 3 minutes combined with a decrease in mean aortic pressure.

Randomization and Blinding

After completing these assessments of flow and function ~3 weeks after the first surgery, animals were randomly assigned to one of the 3 treatment groups: placebo, low concentration GFm or high concentration GFm. By design, the study intended to have a total of 21 animals reach the end of the protocol, 7 in each treatment group, with males and females approximately evenly distributed within each group. 21 envelopes each containing a single treatment group assignment (7 for each group, approximately equally distributed between male and female) were prepared and randomly ordered; each envelope was labeled "male" or "female" so as to guide animal recruitment through the course of the study. On the day prior to the "second surgery" (see next section), an envelope from the stack corresponding to the gender of the animal was randomly chosen from those remaining and was opened by an investigator independent of all other aspects of the investigation. On the day of the second surgery, the assignment group was reviewed by the independent investigator who prepared the treatment solution. All solutions were prepared in a secluded section of the laboratory. All solutions were identical in appearances and were provided to the primary investigators during the surgery approximately 30 minutes before injection. In the event that an animal died at any time before the end of the study or could not complete the study for any reason, the animal was replaced by another animal of the same sex into the same treatment group. As will be detailed, a total of 38 animals were enrolled in order to obtain the 21 survivors who completed the entire study. All animals are accounted for as detailed in Results. All investigators involved in caring for the animals, performing tests, analyzing data or making any interpretations of the test results were completely blinded to group assignment.

Baseline Coronary Angiography and Second Surgery for Intramyocardial Injections Of $Gf_m$ Or Placebo (Second Operation, Op2)

Approximately 21 days after the first surgery and after completing the baseline microsphere and stress echocardiographic studies (study CE1), each dog was anesthetized using the same anesthetic protocol as for the first surgery. Urine samples were obtained using either a urinary catheter or a suprapubic cannula and these were submitted for routine analysis. If possible, the samples were taken prior to angiography. If the bladder was empty, urine had to be withdrawn after surgery. The right femoral artery was surgically exposed and a standard left coronary artery catheter (Cordis Super Torque Plus™ angiographic catheter, JL3.5 6F 100 cm, Ref. Cat. No. 533–618, Cordis Corporation, Miami Fla. or Schneider Guider™ Softip® Guiding Catheter, Judkins Left 2.5 "Classic" JL3.5 6F 100 cm, Model No. 56-JL3.5FC, Schneider (USA) Inc, Pfizer Medical Technology Group, Minneapolis, Minn. or ACS Viking™ Guiding Catheter, Amplatz Left AL 1 6F 100 cm, Guidant Advanced Cardiovascular Systems, Inc., Temecula, Calif.) was introduced under fluoroscopic guidance through the artery into the left main coronary artery. Angiography was performed (Visipaque® (iodixanol), nonionic, iodinated x-ray contrast agent, Nycomed Inc., Princeton, N.J.) using standard views to visualize the left anterior descending artery (LAD) and diagonal vessels. These sequences were recorded on VHS videotape. After completing the angiography, the catheter was withdrawn, the femoral artery ligated, and the skin incision closed.

The chest was then prepared and draped in the usual sterile fashion and the chest opened in the $5^{th}$ intercostal space. At this time the animal was then treated in a blinded manner according to the randomization assignment described above. Animals in Group 1 received intramyocardial $GF_m$ injections at a $GF_m$ concentration of 1 mg/ml, 0.15 ml/injection, 1 injection/cm$^2$ to the LAD region, total of 15–20 injections per heart. Group 2 animals received intramyocardial $GF_m$ injections, at a GFm concentration of 10 mg/ml, 0.15 ml/injection, 1 injection/cm$^2$ to the LAD region, total of 15–20 injections per heart. Group 3 animals received intramyocardial injections of vehicle (1% LMW Povidone) without $GF_m$, 0.15 ml/injection, 1 injection/cm$^2$ to the LAD region, total of 15–20 injections per heart. Injection solutions were prepared by two individuals who were independent of the group of investigators performing the surgeries and follow-up tests. A shallow stitch (4-0 Prolene® taper RB-1 monofilament polypropylene suture, Ethicon, Inc., Somerville, N.J.) was placed over each injection site so that each site could be identified when the heart was removed 6 weeks later. After completing the injections, the heart surface was photographed in order to document the injection site placement. After infiltration of the intercostal musculature with 5 ml of Marcaine® (bupivacaine) the chest was closed in layers (umbilical tape, Ethicon Inc. and 2-0 Vicryl™ taper CT-1 polyglactin sutures, Ethicon Inc., Somerville, N.J.), the pneumothorax was reduced and the animal was allowed to recover.

Each dog received subcutaneous injections of 5-Bromo-2'-Deoxyuridine (BrdU, B-5002, Sigma-Aldrich, St. Louis, Mo.; diluted in 0.9% saline solution, adjusted with KOH to pH 9.0) starting the day before surgery (25 mg/kg), on the day of surgery (15 mg/kg) and days 1, 3, 5, 7, 9, 13 and 20 after surgery (15 mg/kg) as a means of "marking" dividing cells [Boccadoro, 1986 #106] which can be detected using standard immunohistologic techniques.

Physiologic Assessment of Blood Flow and Myocardial Function 3 Weeks After Treatment (Second Conscious Experiment, Ce2)

Between 20 and 22 days (approximately 3 weeks) after the second surgery, blood flow was assessed in the conscious state only during adenosine stress using the third colored microsphere (COLOR 3). Resting blood flow was not measured because there are only 5 different colored microspheres; 2 colors have been used at baseline and 2 are required at the final time point (CE3, see next section). Within the same 20–22 day time window, the resting echocardiogram was repeated. The same protocols for performing microsphere infusions, reference blood sample withdrawals and echocardiography used during the initial evaluations were employed. Blood samples were also obtained for routine analysis in a conventional manner.

Physiologic Assessment of Blood Flow and Myocardial Function 6 Weeks After the Second Surgery (Third Conscious Experiment, Ce3)

Between 40 and 44 days (approximately 6 weeks) after the second surgery, blood flow was assessed at rest and during adenosine stress using the fourth and fifth colored microsphere (COLOR 4 and COLOR 5). Resting and dobutamine stress echocardiographic tests were also performed. Blood flow and echocardiographic tests were performed a minimum of 4 hours apart from each other, preferably on different days within the 40–44 day time window. The same protocols detailed above for performing microsphere infusions, reference blood sample withdrawals, echocardiograms and dobutamine infusion used during the initial evaluations were employed. Blood samples were also obtained to measure a host of chemical and hematologic parameters.

Coronary Angiography Followed by Sacrifice of the Animal and Procurement of Tissue Samples (Terminal Experiment And Sacrifice, Te/Sac)

After completing blood flow and myocardial functional assessments with echocardiography, animals were anesthetized as described above, urine samples were collected in the same manner as during the second surgery and angiography was repeated using the left femoral artery to introduce the coronary catheter. Images were recorded on VHS tape for off-line analysis. After completing the angiography, the animal was sacrificed with an overdose of phenobarbital and the heart was removed. Three transmural tissue blocks, each containing 1 or 2 injection sites (identified by the previously placed epicardial stitches) were isolated in individual transmural tissue blocks. These were cut into three approximately equal thickness sections (epicardial, midwall and endocardial) and placed in 10% neutral buffered formalin (buffered Formalde-Fresh®, low odor 10% Formalin, cat. SF 93-20, Fisher, Fair Lawn, N.J.) for fixation. These sections were taken from the central region of the ischemic territory. The remainder of the heart was cut into approximately 1 gram tissue blocks, with a map of where individual samples were derived (including epicardial and endocardial location; see FIG. 8) and these were submitted together with samples from both kidneys for microsphere analysis. In addition, other organs (lungs, liver, spleen, kidneys, brain, and small intestines) were harvested, weighed and examined grossly and histologically by a certified veterinary pathologist for signs of remote tissue effects of $GF_m$.

After completing the analysis of the study of all results, a table was constructed which summarized the findings of angiography (Angio), histology (Histo), descriptive echocardiographic findings (Echo D), change in echocardiographic wall motion score (Echo WM), change in fractional area shortening from echocardiography ($\Delta$FAC, difference between baseline and final FAC in percentage points) and percent change in blood flow from colored microsphere analysis (CMS, $\Delta$%) were determined. The analysis techniques were as follows:

Angiography was graded on a 3 point semiquantitative scale: 0, no improvement; 1+ mild improvement in distal LAD visualization; 2+ significant improvement in distal LAD visualization. As summarized in the tables, there was a statistically significant improvement in the angiographic score at both high and low concentrations compared to the placebo group. In addition, there was a nearly statistically significant difference between low and high concentration treatments, suggesting a concentration-dependent improvement in blood flow to the distal LAD.

Figure 23:
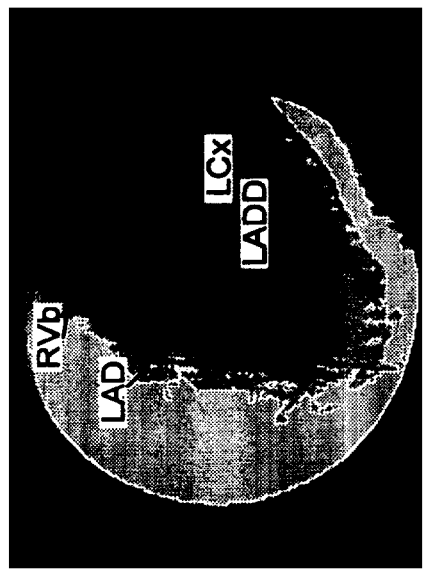
FIGS. 23 and 24 are in vivo angiograms showing blood flood to a representative LAD after placement of an ameroid constrictor on the LAD and occlusion the LAD but before treatment according to the present invention.
Figure 24:
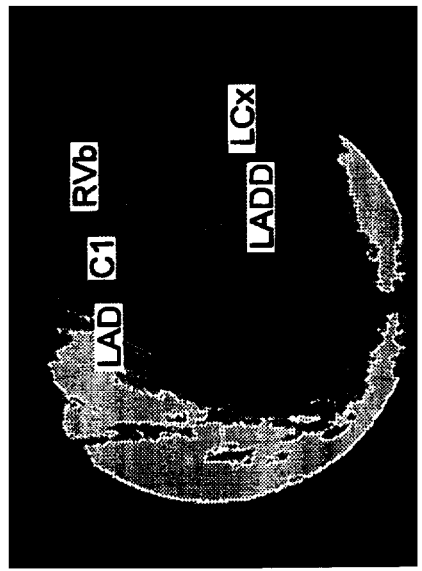
Figure 25:
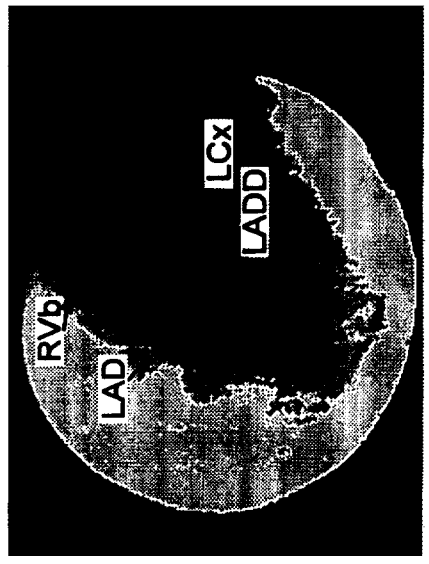
FIGS. 25 and 26 are in vivo angiograms showing blood flood to a representative LAD after placement of an ameroid constrictor on the LAD and occlusion the LAD and six weeks after treatment according to the present invention.
Figure 26:
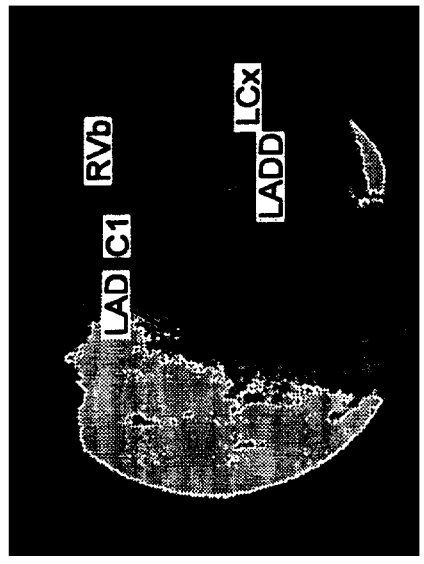

In addition to the graded angiography results given in Table 2, FIGS. 23–26 illustrate the marked improvement in blood flow that resulted from treatment with the inventive composition. In FIGS. 23 and 25, the angiograms are taken at the beginning of the marking process, while the angiograms of FIGS. 24 and 26 are taken after a significant of the radio-opaque marker has been injected. In each of angiograms comprising FIGS. 23, 24, and 25, the visible portion of the LAD is relatively short, indicating that the radio-opaque marker has not entered the LAD. In marked contrast, the LAD is much more visible in FIG. 26, indicating that blood is flowing in the region. Comparing FIGS. 24 and 26, it can be seen that that blood flow past the ameriod constrictor is small in FIG. 24, even well into the injection, whereas blood flow past the ameroid constrictor (via natural bypass mechanisms, i.e. new vessel growth) is greatly improved followed treatment with the inventive composition, as seen in FIG. 26. Hence, it is clear that the administration of an angiogenic factor according to the present invention greatly increases the natural bypass of the LAD or other occluded vessel and allows significant blood flow into a previously ischemic region.

The histologic findings from each animal were reviewed globally and were graded semiquantitatively on a 3 point scale: 0, no significant vascular growth detected; 1+ mild-to-moderate degree of vascular growth detected; 2+, significant amount of vascular growth detected. As summarized in the tables, there was a statistically significant, concentration dependent increase the semi-quantitative grading of vascular growth.

The echocardiograms were analyzed in 3 ways (as summarized in Methods above). EchoD was a semiquantitative descriptive parameter obtained by having an experienced echocardiographer examining changes in the individual wall motion scores between baseline and the final study (CE 3). EchoD was a 3 point scale: –1, worsened wall motion during stress; 0, no change in wall motion during stress; 1+ improved wall motion during stress. This parameter tended to decrease in the high concentration group but this was not statistically significant. Echo WM was the change in the sum of wall motion scores; a lower number for this parameter indicates better function. Similar to the EchoD parameter, there was a slight decrease in function detected in the high concentration group. The third parameter was the change in the percent fractional shortening showed no significant difference between groups.

Microsphere-derived blood flow measurements from all hearts at all conditions measured are shown in Table 1. Prior to any treatment (CE 1), blood flow at rest was similar in all groups and only mildly decreased from the control area, reaching statistical significance only in the Placebo group. During stress, by definition, blood flow in the ischemic and border zones were decreased compared to the control region. During the second conscious experiments (3 weeks after treatment, CE 2), blood flow during stress had not changed significantly in any group; blood flow in the ischemic area was approximately half that in the control region in all groups. Similarly, 6 weeks after treatment blood flow at rest and during stress was similar in all groups and had not changed significantly over time in any group.

TABLE 1

Myocardial Perfusion (ml/min/g tissue)-Results from All animals. (all values are mean ± SEE)

| | | Placebo | Low Conc. GFm | High Conc. GFm |
|---|---|---|---|---|
| Number of animals | | 7 | 7 | 7 |
| CE 1: Rest | Ischemia | 0.76 ± 0.06* | 0.91 ± 0.17 | 0.90 ± 0.10 |
| | Border zone | 0.84 ± 0.11 | 0.92 ± 0.16 | 1.04 ± 0.13 |
| | Control area | 0.94 ± 0.07 | 0.95 ± 0.15 | 1.18 ± 0.12 |

TABLE 1-continued

Myocardial Perfusion (ml/min/g tissue)-Results from All animals. (all values are mean ± SEE)

|  |  | Placebo 7 | Low Conc. GFm 7 | High Conc. GFm 7 |
|---|---|---|---|---|
| CE 1: Stress | Ischemia | 1.66 ± 0.18* | 1.83 ± 0.19* | 1.79 ± 0.15* |
|  | Border zone | 2.55 ± 0.26*# | 2.39 ± 0.29*# | 2.49 ± 0.17*# |
|  | Control area | 4.07 ± 0.53 | 3.70 ± 0.37 | 4.29 ± 0.36 |
| CE 2: Stress | Ischemia | 1.73 ± 0.26* | 2.17 ± 0.19* | 1.79 ± 0.14* |
|  | Border zone | 2.98 ± 0.46*# | 3.00 ± 0.28*# | 2.46 ± 0.38*#=.056 |
|  | Control | 4.41 ± 0.69 | 4.32 ± 0.35 | 3.73 ± 0.53 |
| CE 3: Rest | Ischemia | 0.70 ± 0.05* | 1.07 ± 0.25* | 0.90 ± 0.12* |
|  | Border zone | 0.85 ± 0.08 | 1.16 ± 0.25 | 1.04 ± 0.17 |
|  | Control area | 0.97 ± 0.07 | 1.30 ± 0.26 | 1.22 ± 0.16 |
| CE 3: Stress | Ischemia | 1.90 ± 0.18* | 2.21 ± 0.12* | 1.93 ± 0.19* |
|  | Border zone | 2.81 ± 0.16*# | 3.13 ± 0.16*# | 2.73 ± 0.29*# |
|  | Control area | 3.98 ± 0.37 | 4.51 ± 0.22 | 4.37 ± 0.43 |

*$p < 0.05$ vs. control area, #$p < 0.05$ vs. ischemic area. no significant differences between groups or within groups CE1 vs. CE3. Statistical comparisons done with one way ANOVA with Scheffe post hoc test Lack of uniform maximal vasodilation induced by intravenous adenosine prohibited assessment of blood flow during maximal vasodilatory stress in a large number of animals. As a result, there was a small number values for comparison in each group and there were no statistically significant differences between groups with regard to how blood flow during stress changed in response to treatment.

After unblinding, the results of these measurements were sorted by group and are tabulated in Table 2.

showed that the agent has a concentration-dependent significant effect on vascular growth assessed histologically and by angiographic criteria. There was no significant effect on blood flow during maximal vasodilatory stress, though technical limitations resulted in inclusion of only a small number of studies for the analysis of maximal blood flow rendering the results inconclusive. There was a trend (not statistically significant) towards a slight reduction in regional wall motion score during maximum dobutimine

TABLE 2

Overview of results in each animal sorted by group.

| Group | Name | Nr. | ID # | Angio | Histo | EchoD | EchoWM | ΔFAC | CMS |
|---|---|---|---|---|---|---|---|---|---|
| GFm 1 mg/ml | Leoncavallo | 8 | 3581 | 1+ | 2+ | 1+ | −2 | −15 | n/i |
|  | Monteverdi | 10 | 3879 | 1+ | 1+ | 1+ | −1 | 17 | 1 |
|  | Mozart | 11 | 3605 | 1+ | 1+ | 1− | 0 | −5 | −7 |
|  | Puccini | 16 | 3970 | 1+ | 0/1+[2] | 1+ | −5 | −4 | −1 |
|  | Rossini | 18 | 11767 | 1+ | 0/1+[2] | 1−[4] | 4 | 11 | n/i |
|  | Schumann | 20 | 10568 | 1+ | n/a[2,3] | 1+ | −3 | 1 | −4 |
|  | Lautrec | 36 | 12545 | 2+ | 1+ | 1+ | 4 | −10 | −1 |
|  | Mean |  |  | 1.1 | 1.0 | 0.4 | −0.4 | −4* | −2.4 |
| GFm 10 mg/ml | Vivaldi | 25 | 4018 | 1+ | 1+[3] | 1+ | −3 | 5 | −2 |
|  | Boticelli | 27 | 11190 | 2+ | 1+ | 1− | 4 | 2 | 1 |
|  | Dali | 29 | 11187 | 2+ | 2+ | 0 | 2 | −10 | −7 |
|  | Degas | 30 | 4070 | 2+ | 2+ | 0 | −1 | −6 | n/i |
|  | Gauguin | 32 | 12311 | 2+ | 2+ | 1− | 4 | −4 | n/i |
|  | Matisse | 38 | 4209 | 0 | 2+ | 1− | 5 | 3 | n/i |
|  | Michelangelo | 39 | 11745 | 2+ | 2+ | 1− | 4 | −5 | 6 |
|  | Mean |  |  | 1.6 | 1.7 | −0.4 | 2.1 | −4* | −0.5 |
| Placebo | Dvorak | 5 | 10213 | 0 | 0 | 1+ | −4 | −3 | n/i |
|  | Gershwin | 6 | 3711 | 1+ | 0/1+[1] | 1+ | −4 | 1 | 6 |
|  | Mussorgsky | 12 | 11334 | 1+ | 1+ | 1− | −1 | 15 | n/i |
|  | Offenbach | 13 | 3889 | 1+ | 0 | 1+ | −4 | 0 | 5 |
|  | Tchaikovsky | 23 | 4130 | 0 | 0 | 1+ | −4 | 7 | n/i |
|  | Klimt | 35 | 4143 | 0 | 0 | 0 | 0 | 54 | −14 |
|  | Lichtenstein | 37 | 4023 | 0 | 0 | 1+ | 0 | −2 | 18 |
|  | Mean |  |  | 0.4 | 0.2 | 0.6 | −2.4 | 1* | 3.75 |

*Median used instead of mean because of large non–normal distribution. N/i, not included. See
[1]histology suggestive of presence of myocardial infarction
[2]technical problem with histologic staining
[3]histology suggestive of myocardial infarction alone
[4]The score for this animal was initially inadvertently entered onto the table sent to the Sponsor as "0"; this should have been entered as "1−", as it now appears In summary, the general results of this prospective, blinded, multifaceted assessment of the effects of GFm stress, though global resting function was not influenced by treatment. Nonetheless, there is histologic and angiographic evidence of significant vascular growth, though LV function during stress and blood flow by color microsphere analysis did not improve.

Administration of angiogenic factors in accordance with the present invention has several advantages over the alternative methods for inducing angiogenesis, such as inflammation resulting from laser injury. The growth factors of the present invention can be delivered in a minimally invasive manner to ischemic tissues either through a thoracotomy or percutaneous catheterization without the use of expensive equipment. In addition, the process for manufacturing the present angiogenic factors can be readily scaled up to a commercial production scale. A further advantage is that the proteins are kept in solution during the purification steps and exhibit little deterioration during the production process. Another advantage is that the resultant mixture of proteins can be used directly, without the mixing that may be required with proteins produced by other processes.

While the present angiogenic factor and methods for producing and administering it have been described according to a preferred embodiment, it will be understood that departures can be made from some aspects of the foregoing description without departing from the scope of the invention.

What is claimed is:

1. A method of promoting natural bypass in a mammal to provide increased blood flow to tissue served by an occluded or partly occluded vessel, comprising administering to the mammal a mixture of proteins derived from ground bone.

2. The method according to claim 1 wherein the mixture of proteins derived from ground bone comprises at least two growth factors selected from the group consisting of bone morphogenic protein-2 (BMP-2), bone morphogenic protein-3 (BMP-3), bone morphogenic protein-4 (BMP-4), bone morphogenic protein-5 (BMP-5), bone morphogenic protein-6 (BMP-6), bone morphogenic protein-7 (BMP-7), transforming growth factor β1 (TGF-β1), transforming growth factor β2 (TGF-β2), transforming growth factor β3 (TGF-β3) and fibroblast growth factor 1 (FGF-1).

3. The method of claim 1, wherein the mammal is a human.

4. The method of claim 1, wherein the mixture is administered subcutaneously, intramuscularly, or intravenously.

5. The method of claim 1, wherein the mixture is administered discretely or continuously.

6. The method of claim 1, wherein said mixture further comprises a growth factor selected from the group consisting of insulin-like growth factor-1 (IGF-1), epidermal growth factor (EGF), hepatocyte growth factor (HGF), transforming growth factor α(TGF-α), and platelet-derived growth factor (PDGF).

7. The method of claim 1, wherein the mixture further comprises a preservative or an adjuvant.

8. A method of promoting natural bypass in a mammal to provide increased blood flow to tissue served by an occluded or partly occluded vessel, comprising administering to the mammal a mixture of proteins derived from ground bone, wherein the mixture comprises BMP-2, BMP-3, BMP-7, TGF-β, and FGF.

9. A method of promoting natural bypass in a mammal to provide increased blood flow to tissue served by an occluded or partly occluded vessel, comprising administering to the mammal a mixture of proteins derived from ground bone, wherein the mixture is derived by:
 (i) grinding mammalian bone, to produce ground bone;
 (ii) cleaning the ground bone, to produce cleaned ground bone;
 (iii) demineralizing the cleaned ground bone, to produce demineralized cleaned ground bone;
 (iv) extracting protein from the demineralized cleaned ground bone using a protein denaturant to yield extracted protein;
 (v) ultrafiltering the extracted protein to separate out high molecular weight proteins;
 (vi) ultrafiltering the extracted protein to separate out low molecular weight proteins;
 (vii) transferring the extracted protein to a non-ionic denaturant;
 (viii) subjecting the extracted protein to an anion exchange process;
 (ix) subjecting the extracted protein to a cation exchange process; and
 (x) subjecting the extracted protein to a reverse phase HPLC process.

10. The method of claim 9, wherein the mammalian bone is bovine bone.

11. A method of promoting vessel growth to heal a heart artery that has been partly or fully occluded, comprising administering to the heart a mixture of proteins derived from ground bone.

12. The method according to claim 11 wherein the mixture of proteins derived from ground bone comprises at least two growth factors selected from the group consisting of bone morphogenic protein-2 (BMP-2), bone morphogenic protein-3 (BMP-3), bone morphogenic protein-4 (BMP-4), bone morphogenic protein-5 (BMP-5), bone morphogenic protein-6 (BMP-6), bone morphogenic protein-7 (BMP-7), transforming growth factor β1 (TGF-β1), transforming growth factor β2 (TGF-β2), transforming growth factor β3 (TGF-β3), and fibroblast growth factor 1 (FGF-1).

13. The method of claim 11, wherein the heart is a human heart.

14. The method of claim 11, wherein the mixture is administered subcutaneously, intramuscularly, or intravenously.

15. The method of claim 11, wherein the mixture is administered discretely or continuously.

16. The method of claim 11, wherein the mixture further comprises a growth factor selected from the group consisting of insulin-like growth factor-1 (IGF-1), epidermal growth factor (EGF), hepatocyte growth factor (HGF), transforming growth factor α (TGF-α), and platelet-derived growth factor (PDGF).

17. The method of claim 11, wherein the mixture further comprises a preservative or an adjuvant.

18. The method of claim 11, wherein the mixture comprises BMP-2, BMP-3, BMP-7, TGF-β, and FGF.

19. The method of claim 11, wherein said mixture is obtained by:
 (i) grinding mammalian bone, to produce ground bone;
 (ii) cleaning the ground bone, to produce cleaned ground bone;
 (iii) demineralizing the cleaned ground bone, to produce demineralized cleaned ground bone;
 (iv) extracting protein from the demineralized cleaned ground bone using a protein denaturant to yield extracted protein;
 (v) ultrafiltering the extracted protein to separate out high molecular weight proteins;
 (vi) ultrafiltering the extracted protein to separate out low molecular weight proteins;
 (vii) transferring the extracted protein to a non-ionic denaturant;
 (viii) subjecting the extracted protein to an anion exchange process;
 (ix) subjecting the extracted protein to a cation exchange process; and
 (x) subjecting the extracted protein to a reverse phase HPLC process.

20. The method of claim 19, wherein the mammalian bone is bovine bone.

21. A method of treating ischemic tissue damage in a mammal, said method comprising at least the step of: administering to said ischemic tissue a composition that comprises a mixture of proteins derived from ground bone.

22. The method according to claim 21 wherein the mixture of proteins derived from ground bone comprises at least two growth factors selected from the group consisting of bone morphogenic protein-2 (BMP-2), bone morphogenic protein-3 (BMP-3), bone morphogenic protein-4 (BMP-4), bone morphogenic protein-5 (BMP-5), bone morphogenic protein-6 (BMP-6), bone morphogenic protein-7 (BMP-7), transforming growth factor β1 (TGF-β1), transforming growth factor β2 (TGF-β2), transforming growth factor β3 (TGF-β3), and fibroblast growth factor 1 (FGF-1).

23. The method of claim 21, wherein said ischemic tissue is human tissue.

24. The method of claim 21, wherein said composition is administered subcutaneously, intramuscularly, or intravenously.

25. The method of claim 21, wherein said composition is administered discretely or continuously.

26. The method of claim 21, wherein said mixture further comprises a growth factor selected from the group consisting of insulin-like growth factor-1 (IGF-1), epidermal growth factor (EGF), hepatocyte growth factor (HGF), transforming growth factor α (TGF-α), and platelet-derived growth factor (PDGF).

27. The method of claim 21, wherein said composition further comprises a preservative or an adjuvant.

28. The method of claim 21, wherein said mixture comprises BMP-2, BMP-3, BMP-7, TGF-β, and FGF.

29. The method of claim 21, wherein said mixture is obtained by:
 (i) grinding mammalian bone, to produce ground bone;
 (ii) cleaning the ground bone, to produce cleaned ground bone;

(iii) demineralizing the cleaned ground bone, to produce demineralized cleaned ground bone;
(iv) extracting protein from the demineralized cleaned ground bone using a protein denaturant to yield extracted protein;
(v) ultrafiltering the extracted protein to separate out high molecular weight proteins;
(vi) ultrafiltering the extracted protein to separate out low molecular weight proteins;
(vii) transferring the extracted protein to a non-ionic denaturant;
(viii) subjecting the extracted protein to an anion exchange process;
(ix) subjecting the extracted protein to a cation exchange process; and
(x) subjecting the extracted protein to a reverse phase HPLC process.

30. The method of claim 29, wherein the mammalian bone is bovine bone.

31. The method of claim 21, wherein said bone is mammalian bone.

32. The method of claim 31, wherein said mammalian bone is bovine bone.

* * * * *